US010130310B2

(12) United States Patent
Alpert et al.

(10) Patent No.: US 10,130,310 B2
(45) Date of Patent: Nov. 20, 2018

(54) BEDSIDE CONTROLLER FOR ASSESSMENT OF VESSELS AND ASSOCIATED DEVICES, SYSTEMS, AND METHODS

(71) Applicant: Volcano Corporation, San Diego, CA (US)

(72) Inventors: Howard David Alpert, El Dorado Hills, CA (US); David Anderson, Temecula, CA (US); Asher Cohen, Sacramento, CA (US); Fergus Merritt, Escondido, CA (US); Meng Lim, San Diego, CA (US)

(73) Assignee: VOLCANO CORPORATION, San Diego, CA (US)

( * ) Notice: Subject to any disclaimer, the term of this patent is extended or adjusted under 35 U.S.C. 154(b) by 532 days.

(21) Appl. No.: 14/850,720

(22) Filed: Sep. 10, 2015

(65) Prior Publication Data

US 2016/0073972 A1    Mar. 17, 2016

Related U.S. Application Data

(60) Provisional application No. 62/049,265, filed on Sep. 11, 2014.

(51) Int. Cl.
*A61B 5/026* (2006.01)
*A61B 5/0215* (2006.01)
(Continued)

(52) U.S. Cl.
CPC ............ *A61B 5/7445* (2013.01); *A61B 5/026* (2013.01); *A61B 5/02007* (2013.01);
(Continued)

(58) Field of Classification Search
CPC ............. A61B 5/7445; A61B 5/02007; A61B 5/02158; A61B 5/026; A61B 5/7425; A61B 5/743; A61B 5/7475
(Continued)

(56) References Cited

U.S. PATENT DOCUMENTS 7,134,994 B2 * 11/2006 Alpert .................. A61B 5/0215
600/300
8,754,865 B2    6/2014 Merritt et al.
(Continued)

FOREIGN PATENT DOCUMENTS

WO    WO2012/093260    1/2012
WO    WO2012/093266    1/2012
(Continued)

*Primary Examiner* — Navin Natnithithadha

(57) ABSTRACT

Devices, systems, and methods for evaluating a vessel of a patient are provided. The method includes outputting, to a touch-sensitive display of a bedside controller, a screen display including: a visual representation of a first pressure ratio of pressure measurements obtained by first and second instruments positioned within a vessel while the second instrument is moved from a distal position to a proximal position relative a stenosis and the first instrument remains stationary; and a first proximal pressure waveform and a first distal pressure waveform; receiving, through the touch-sensitive display of the bedside controller, a user touch input on the first proximal pressure waveform and/or the first distal pressure waveform identifying a time at which pressure measurements were obtained; and modifying the screen display, in response to the user touch input, to further include a visual representation of the obtained pressure measurements corresponding to the identified time.

20 Claims, 18 Drawing Sheets

(51) Int. Cl.
*A61B 5/00* (2006.01)
*A61B 5/02* (2006.01)
(52) U.S. Cl.
CPC .......... *A61B 5/02158* (2013.01); *A61B 5/743* (2013.01); *A61B 5/7425* (2013.01); *A61B 5/7475* (2013.01)
(58) Field of Classification Search
USPC ................. 600/481, 483–486, 488, 490–499
See application file for complete search history.

(56) References Cited

U.S. PATENT DOCUMENTS

| | | | | |
|---|---|---|---|---|
| 9,026,384 B2* | 5/2015 | Davies | ............... | A61B 5/02007 |
| | | | | 702/182 |
| 9,339,348 B2* | 5/2016 | Davies | ................... | A61B 5/742 |
| 9,364,153 B2* | 6/2016 | Merritt | ................. | A61B 5/7278 |
| 9,775,524 B2* | 10/2017 | Davies | ............... | A61B 5/02007 |
| 2003/0216621 A1* | 11/2003 | Alpert | ................. | A61B 5/0215 |
| | | | | 600/300 |
| 2007/0060822 A1* | 3/2007 | Alpert | ................. | A61B 5/0215 |
| | | | | 600/481 |
| 2010/0234698 A1* | 9/2010 | Manstrom | ............. | A61M 5/007 |
| | | | | 600/301 |
| 2013/0046190 A1 | 2/2013 | Davies | | |
| 2013/0345574 A1* | 12/2013 | Davies | ............... | A61B 5/02007 |
| | | | | 600/486 |
| 2014/0135633 A1 | 5/2014 | Anderson et al. | | |
| 2014/0258743 A1 | 9/2014 | Nool | | |
| 2015/0025330 A1 | 1/2015 | Davies | | |
| 2015/0025398 A1 | 1/2015 | Davies | | |
| 2015/0080749 A1* | 3/2015 | Anderson | ............ | A61B 5/0215 |
| | | | | 600/483 |
| 2015/0230713 A1 | 8/2015 | Merritt et al. | | |
| 2015/0238096 A1 | 8/2015 | Merritt et al. | | |

FOREIGN PATENT DOCUMENTS

| | | |
|---|---|---|
| WO | WO2013/028612 | 8/2012 |
| WO | WO2012/154335 | 11/2012 |

* cited by examiner

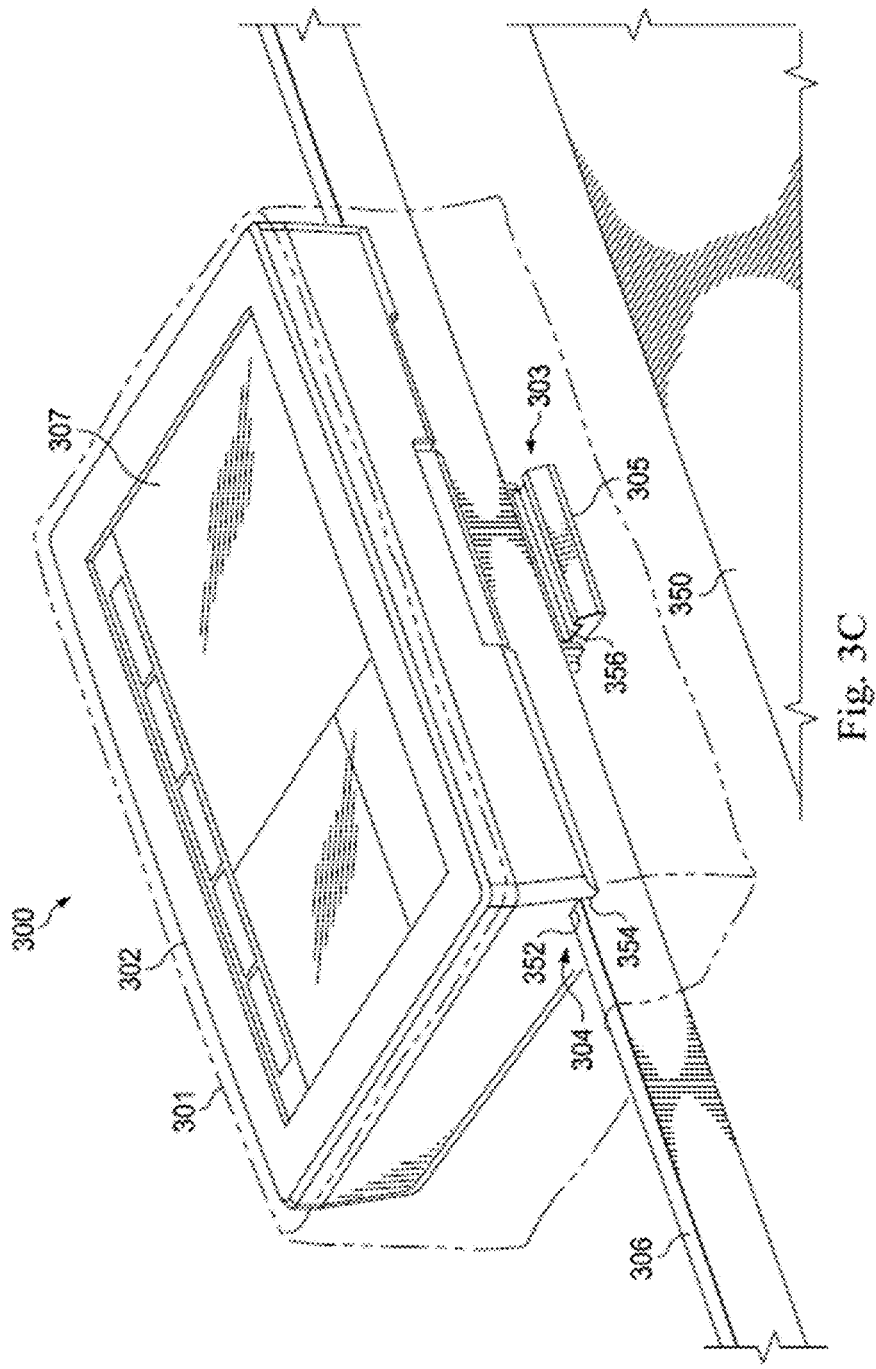

BEDSIDE CONTROLLER FOR ASSESSMENT OF VESSELS AND ASSOCIATED DEVICES, SYSTEMS, AND METHODS

CROSS REFERENCE TO RELATED APPLICATIONS

The present application claims priority to and the benefit of the U.S. Provisional Patent Application No. 62/049,265, filed Sep. 11, 2014, which is hereby incorporated by reference in its entirety.

TECHNICAL FIELD

The present disclosure relates generally to the assessment of vessels using a bedside controller. For example, some embodiments of the present disclosure are suited for assessing the severity of a blockage or other restriction to the flow of fluid through a vessel, such as a stenosis of a human blood vessel, by analyzing medical sensing data collected from the vessel using a touch-sensitive display of the bedside controller.

BACKGROUND

Innovations in diagnosing and verifying the level of success of treatment of disease have progressed from solely external imaging processes to include internal diagnostic processes. In addition to traditional external image techniques such as X-ray, MRI, CT scans, fluoroscopy, and angiography, small sensors may now be placed directly in the body. For example, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy. Traditionally, many of these procedures are carried out by a multitude of physicians and clinicians, where each performs an assigned task. For example, a physician may stand next to a patient in the sterile field and guide the insertion and pull back of a medical sensing catheter. A clinician near the physician may control the procedure workflow with a controller, for example by starting and stopping the acquisition of medical data. Further, once medical data has been acquired, a second clinician in an adjacent control room working at a desktop computer may analyze the data, such as by reviewing quantities calculated from the acquired data. Typically, the physician in the catheter lab and the clinician in the control room must communicate in order to acquire and analyze the relevant medical data. This may lengthen the time of the procedure, increase the cost of the procedure, and may lead to errors due to miscommunication or clinician inexperience.

One exemplary type of procedure involves pressure measurements within a blood vessel. A currently accepted technique for assessing the severity of a stenosis in the blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance predominantly by reducing the microcirculation resistance associated with the systolic portion of the heart cycle to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

Accordingly, there remains a need for improved devices, systems, and methods for assessing the severity of a blockage in a vessel and, in particular, a stenosis in a blood vessel. In that regard, there remains a need for improved devices, systems, and methods for assessing the severity of a stenosis in the coronary arteries that do not require the administration of hyperemic agents. There also remains a need for improved devices, systems, and methods for providing visual depictions of vessel that allow assessment of the vessel and, in particular, any stenosis or lesion of the vessel. Further, there remains a need for assessing the severity of a stenosis and for providing visual depictions of the vessel in an efficient manner.

SUMMARY

Embodiments of the present disclosure are configured to efficiently assess the severity of a blockage in a vessel and, in particular, a stenosis in a blood vessel using a bedside controller. In some particular embodiments, the devices, systems, and methods of the present disclosure are configured to provide screen displays that allow assessment of the vessel and, in particular, any stenosis or lesion of the vessel on a touch-sensitive display of the bedside controller. Vessel data can be efficiently assessed using touch inputs received on the bedside controller.

In an exemplary aspect, the present disclosure is directed to a method of evaluating a vessel of a patient. The method includes outputting, to a touch-sensitive display of a bedside controller, a screen display including: a visual representation of a first pressure ratio of pressure measurements obtained by first and second instruments positioned within a vessel while the second instrument is moved longitudinally through the vessel from a first position distal of a stenosis of the vessel to a second position proximal of the stenosis and the first instrument remains stationary within the vessel; and a first proximal pressure waveform and a first distal pressure waveform of the obtained pressure measurements; receiving, through the touch-sensitive display of the bedside controller, a user touch input on at least one of the first proximal pressure waveform and the first distal pressure waveform identifying a time at which pressure measurements were obtained; and modifying the screen display, in response to the user touch input, to further include a visual representation of the obtained pressure measurements corresponding to the identified time.

In some aspects, the visual representation of the obtained pressure measurements corresponding to the identified time is displayed at a location proximate the at least a portion of the first pressure waveform defined by a point of initial contact with the touch-sensitive display. In some aspects, the visual representation of the obtained pressure measurements corresponding to the identified time includes a numerical value of the obtained pressure measurements at the identified time. In some aspects, the visual representation of the obtained pressure measurements corresponding to the identified time includes a first pressure ratio of the obtained pressure measurements at the identified time. In some aspects, the visual representation of the obtained pressure measurements corresponding to the identified time includes a second pressure ratio of the obtained pressure measurements at the identified time, wherein the second pressure ratio is calculated differently than the first pressure ratio. In some aspects, the visual representation of the obtained pressure measurements corresponding to the identified time includes a numerical value of the obtained pressure measurements at the identified time, a first pressure ratio of the obtained pressure measurements at the identified time, and a second pressure ratio of the obtained pressure measurements at the identified time, wherein the second pressure ratio is calculated differently than the first pressure ratio. In some aspects, the screen display includes a second proximal pressure waveform and a second distal pressure waveform of the obtained pressure measurements, wherein the second proximal and distal pressure waveforms illustrates the obtained pressure measurements over a greater amount of time compared to the first proximal and distal pressure waveforms. In some aspects, the screen display includes an overlay positioned over a portion of the second proximal and distal pressure waveforms, the overlay illustrating a portion of the obtained pressure measurement represented in the first proximal and distal pressure waveforms. In some aspects, the method further includes receiving, through the touch-sensitive display of the bedside controller, a user touch input on the overlay to move the overlay to be positioned over a different portion of the second proximal and distal pressure waveforms; and modifying the screen display, in response to the user touch input, such that the at least a portion of the first proximal and distal pressure waveforms include the obtained pressure measurements corresponding to the position of the overlay over the different portion of the second proximal and distal pressure waveforms. In some aspects, the screen display includes a plurality of pressure ratios of the obtained pressure measurements, each of the plurality of pressure ratios separated by a fixed interval. In some aspects, the screen display includes numerical values of the obtained pressure measurements. In some aspects, the visual representation of a first pressure ratio of the obtained pressure measurements includes a numerical value. In some aspects, the screen display includes a second pressure ratio of the obtained pressure measurements, wherein the second pressure ratio is calculated differently than the first pressure ratio. In some aspects, the screen display includes visual representation of a difference in the pressure measurements.

In an exemplary aspect, the present disclosure is directed to a system for evaluating a vessel of a patient, comprising: a first instrument sized and shaped for introduction into the vessel of the patient; a second instrument sized and shaped for introduction into the vessel of the patient; a bedside controller comprising a touch-sensitive display, the bedside controller being configured to display a screen display and to receive user touch inputs on the touch-sensitive display; and a processing system communicatively coupled to the first and second instruments and the bedside controller, the processing system configured to: receive pressure measurements from the first and second instruments positioned within a vessel while the second instrument is moved longitudinally through the vessel from a first position distal of a stenosis of the vessel to a second position proximal of the stenosis and the first instrument remains stationary within the vessel; output, to the touch-sensitive display of the bedside controller, the screen display including: a visual representation of a pressure ratio of the obtained pressure measurements; and a first proximal pressure waveform and a first distal pressure waveform of the obtained pressure measurements; receive a signal from the bedside controller in response to a user touch input received at the touch-sensitive display, the user touch input identifying a time at which pressure measurements were obtained on at least one of the first proximal pressure waveform and the first distal proximal pressure waveform; and modify the screen display, in response to the received signal, to further include a visual representation of the obtained pressure measurements corresponding to the identified time.

In some aspects, wherein the visual representation of the obtained pressure measurements corresponding to the identified time includes a numerical value of the obtained pressure measurements at the identified time and a numerical value of a first pressure ratio of the obtained pressure measurements at the identified time. In some aspects, the visual representation of the obtained pressure measurements corresponding to the identified time further includes a numerical value of a second pressure ratio of the obtained pressure measurements at the identified time, wherein the second pressure ratio is calculated differently than the first pressure ratio. In some aspects, the processing system is configured to output the screen display further including: a second proximal pressure waveform and a second distal pressure waveform of the obtained pressure measurements, the second proximal and distal pressure waveforms illustrating the obtained pressure measurements over a greater amount of time compared to the first proximal and distal pressure waveforms; and an overlay positioned over a portion of the second proximal and distal pressure waveforms, the overlay illustrating a portion of the obtained pressure measurements represented in the first proximal and distal pressure waveforms. In some aspects, the processing system is further configured to: receive a signal from the bedside controller in response to a user touch input received at the touch-sensitive display, the user touch input moving the overlay to be positioned over a different portion of the second pressure waveform; and modify the screen display, in response to the received signal, such that the at least a portion of the first waveform includes the obtained pressure measurements corresponding to the position of the overlay over the different portion of the second pressure waveform. In some aspects, the processing system is configured to output the screen display further including: a plurality of pressure ratios of the obtained pressure measurements, each of the plurality of pressure ratios separated by a fixed interval.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 3C is a diagrammatic perspective view of the bedside controller of FIGS. 3A and 3B mounted to a bed rail.

DETAILED DESCRIPTION

Figure 1:
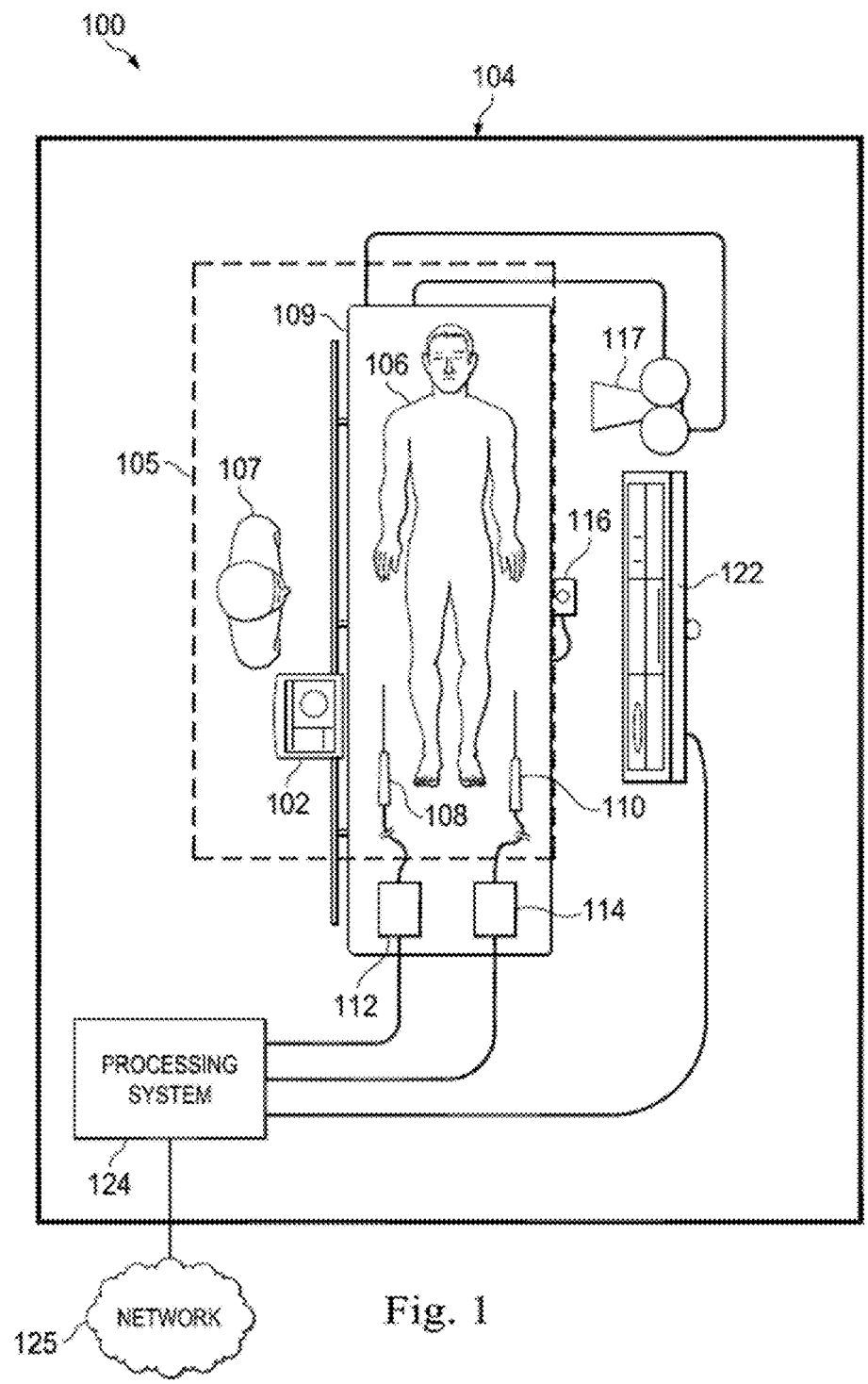
FIG. 1 is a schematic drawing depicting a medical sensing system including a bedside controller according to one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic drawing depicting a medical sensing system 100 including a bedside controller 102 according to one embodiment of the present disclosure. In general, the medical sensing system 100 provides for coherent integration and consolidation of multiple forms of acquisition and processing elements designed to be sensitive to a variety of methods used to acquire and interpret human biological physiology and morphological information. More specifically, in system 100, the bedside controller 102 is a touch-enabled, integrated computing device for the acquisition, control, interpretation, measurement, and display of medical sensing data. In the illustrated embodiment, the bedside controller 102 is a tablet-style touch-sensitive computer that provides user controls and diagnostic images on a single surface. In the medical sensing system 100, the bedside controller 102 is operable to present workflow control options and patient image data via graphical user interfaces (GUIs) corresponding to a plurality of medical sensing modalities. The bedside controller 102 will be described in greater detail in association with FIGS. 3A, 3B, and 4.

In the illustrated embodiment, the medical sensing system 100 is deployed in a catheter lab 104. The catheter lab 104 may be used to perform on a patient 106 any number of medical sensing procedures alone or in combination such as, by way of example and not limitation, angiography, intravascular ultrasound (IVUS), virtual histology (VH), forward looking IVUS (FL-IVUS), intravascular photoacoustic (IVPA) imaging, pressure, fractional flow reserve (FFR) determination, flow velocity, flow volume, coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. Catheter lab 104 can also conduct medical sensing procedures associated with Instant Wave-Free Ratio™ Functionality (iFR® Functionality) (both trademarks of Volcano Corp.) and those disclosed in U.S. patent application Ser. No. 13/460,296 filed Apr. 30, 2012, now published as U.S. Patent Application Publication No. US 2013-0046190 A1 on Feb. 21, 2013 and entitled "DEVICES, SYSTEMS, AND METHODS FOR ASSESSING A VESSEL," hereby incorporated by reference in its entirety, which discloses the use of pressure ratios that are available without application of a hyperemic agent. Further, medical sensing procedures associated with compensated Pd/Pa ratios suitable for estimating iFR®, FFR, and/or other accepted diagnostic pressure ratios as disclosed in U.S. Provisional Patent Application No. 62/024,005, filed Jul. 14, 2014 and entitled "DEVICES, SYSTEMS, AND METHODS FOR TREATMENT OF VESSELS," which is hereby incorporated by reference in its entirety, can be conducted in the catheter lab 104. In addition to controlling medical sensing systems, the bedside controller may be used to cooperate with and control medical treatment systems such as, for example but without limitation, those used for stent placement, coil embolism, ablation therapy, kidney stone treatments, basket placement in a cystoscopy, tumor removal, and chemical therapies. The catheter lab 104 further includes a sterile field 105 that encompasses the portions of the catheter lab surrounding the patient 106 on a procedure table 109 and a clinician 107, who may perform any number of medical sensing procedures or treatments. As shown in FIG. 1, the bedside controller 102 may be positioned within the sterile field 105 and may be utilized by the clinician 107 to control a workflow of a medical sensing procedure or treatment being performed on the patient 106. For example, the clinician 107 may initiate the procedure workflow, watch real-time medical sensing data, such as pressure measurements (e.g., visual representations of pressure data, such as pressure waveforms), obtained during the procedure, and interact with the obtained medical sensing data using the bedside controller 102 inside of the sterile field 105. In alternative embodiments, the bedside controller 102 may be utilized outside of the sterile field 105, for instance, in other locations within the catheter lab 104 or in a control room adjacent to the catheter lab. A method of utilizing the bedside controller 102 to control a medical sensing workflow or treatment workflow will be discussed in greater detail below. In some embodiments, the medical sensing system 100 can be implemented as the system 850 (FIG. 8), described below. In some embodiments, one or more components of the system 850 can be implemented in the medical sensing system 100.

In the embodiment illustrated in FIG. 1, the medical sensing system 100 additionally includes a number of interconnected medical sensing-related tools in the catheter lab 104 to facilitate a pressure-sensing workflow procedure, such as a medical sensing device 108 and a medical sensing device 110, and a processing system 124. The medical sensing devices 108 and 110 can include pressure monitoring elements. Some embodiments of the medical sensing system 100 can include an patient interface module (PIM) 112 communicatively coupled to the medical sensing device 108, PIM 114 communicatively coupled to the medical sensing device 110, an electrocardiogram (ECG) device 116, an angiogram system 117, and a boom display 122. The bedside controller 102, PIMs 112 and 114, ECG device 116, angiography system 117, and boom display 122 are communicatively coupled to the processing system 124. In some embodiments, the medical sensing devices 108 and 110 can include imaging elements to facilitate an imaging workflow. In one embodiment, the processing system 124 is a computer workstation with the hardware and software to acquire, process, and display medical sensing data, but in other embodiments, the processing system may be any other type of computing system operable to process medical sensing data. For example, during a pressure-sensing workflow, the processing system 124 is operable to accept raw pressure data from the medical sensing devices 108 and 110 and/or the PIMs 112 and 114, transform the pressure data into screen displays including, e.g., visual representations such as pressure waveforms, numerical values, computed values, etc., and make the screen display available to the bedside controller 124, so that they may be displayed to the clinician 107 for analysis. In the embodiments in which the processing system 124 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller. Further, the processing system 124 is communicatively coupled to a data network 125. In the illustrated embodiment, the data network 125 is a TCP/IP-based local area network (LAN), however in other embodiments, it may utilize a different protocol such as Synchronous Optical Networking (SONET), or may be a wide area network (WAN). The processing system 124 may connect to various resources via the network 125, such as a Digital Imaging and Communications in Medicine (DICOM) system, a Picture Archiving and Communication System (PACS), and a Hospital Information System. The processing system 124 can be similar to a multi-modality processing system that processes medical sensing data disclosed in U.S. Pat. No. 8,754,865, entitled "MEDICAL MEASURING SYSTEM AND METHOD" and issued on Jun. 17, 2014, and U.S. Patent Application No. 61/473,570, filed on Apr. 8, 2011 entitled "MULTI-MODALITY MEDICAL SENSING SYSTEM AND METHOD" and published as PCT Patent Application Publication No. WO/2012/154335 on Nov. 15, 2012, both of which are hereby incorporated by reference herein in their entireties.

In the medical sensing system 100, the PIM 112 and PIM 114 are operable to respectively receive medical sensing data collected from the patient 106 by the medical sensing device 108 and medical sensing device 110 and are operable to transmit the received data to the processing system 124. In one embodiment, the PIM 112 and PIM 114 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. Additionally, the ECG device 116 is operable to transmit electrocardiogram signals or other hemodynamic data from patient 106 to the processing system 124. To aid the clinician in data capture, the bedside controller 102 is operable to display the ECG data alongside medical sensing data. Further, in some embodiments, the processing system 124 may be operable to synchronize data collection with the catheters 108 and 110 using ECG signals from the ECG 116. Further, the angiogram system 117 is operable to collect x-ray, computed tomography (CT), or magnetic resonance images (MRI) of the patient 106 and transmit them to the processing system 124. After the x-ray, CT, or MRI data has been processed into human-readable images by the processing system 124, the clinician 107 may navigate the GUI on the bedside controller 124 to retrieve the images from the processing system 124 and display them on the controller. In some embodiments, the processing system 124 may co-register image data from angiogram system 117 (e.g. x-ray data, MRI data, CT data, etc.) with sensing data from the and catheters 108 and 110. As one aspect of this disclosure, the co-registration may be performed to generate three-dimensional images with the sensing data. Such co-registered 3-D images data may be viewable on the bedside controller 124. In one embodiment, a clinician may rotate, zoom, and otherwise manipulate such 3-D images on the bedside controller 102 using simultaneous touch inputs (i.e. multi-touch) and gestures.

Additionally, in the illustrated embodiment of FIG. 1, medical sensing tools in system 100, are communicatively coupled to the processing system 124 via a wired connection such as a standard copper link or a fiber optic link. Specifically, the bedside controller 124 may be communicatively and/or electrically coupled to the processing system 124 via a Universal Serial Bus (USB) connection, a Power-over-Ethernet connection, a Thunderbolt connection, a FireWire connection, or some other high-speed data bus connection.

Figure 2:
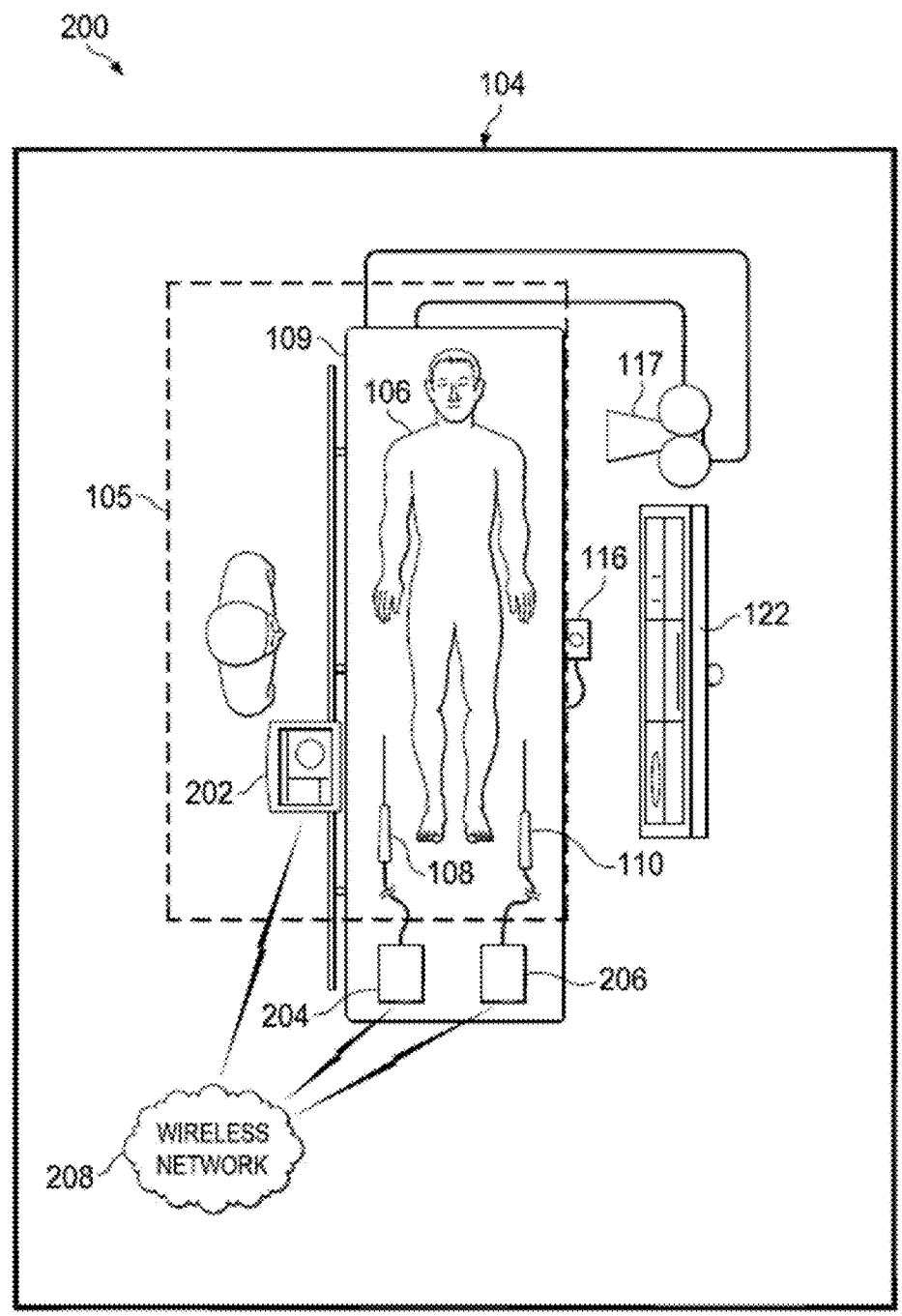
FIG. 2 is a schematic drawing depicting a medical sensing system including a wireless bedside controller according to another embodiment of the present disclosure.

However, in an alternative embodiment, such as that shown in FIG. 2, the medical sensing tools may communicate wirelessly. In that regard, FIG. 2 is a schematic drawing depicting a medical sensing system 200 including a wireless bedside controller 202 according to another embodiment of the present disclosure. The medical sensing system 200 is similar to the system 100 of FIG. 1 but the medical sensing tools including the wireless bedside controller 202, a wireless PIM 204, and a wireless PIM 206 communicate with a wireless network 208 via wireless networking protocols. For example, the bedside controller 202 may send and receive workflow control parameters, medical sensing images, and measurement data to and from a remote processing system via IEEE 802.11 Wi-Fi standards, Ultra Wide-Band (UWB) standards, wireless FireWire, wireless USB, Bluetooth, or another high-speed wireless networking standard. Such wireless capability allows the clinician 107 to more freely position the bedside controller 202 inside or outside of the sterile field 105 for better workflow management.

Figure 3A:
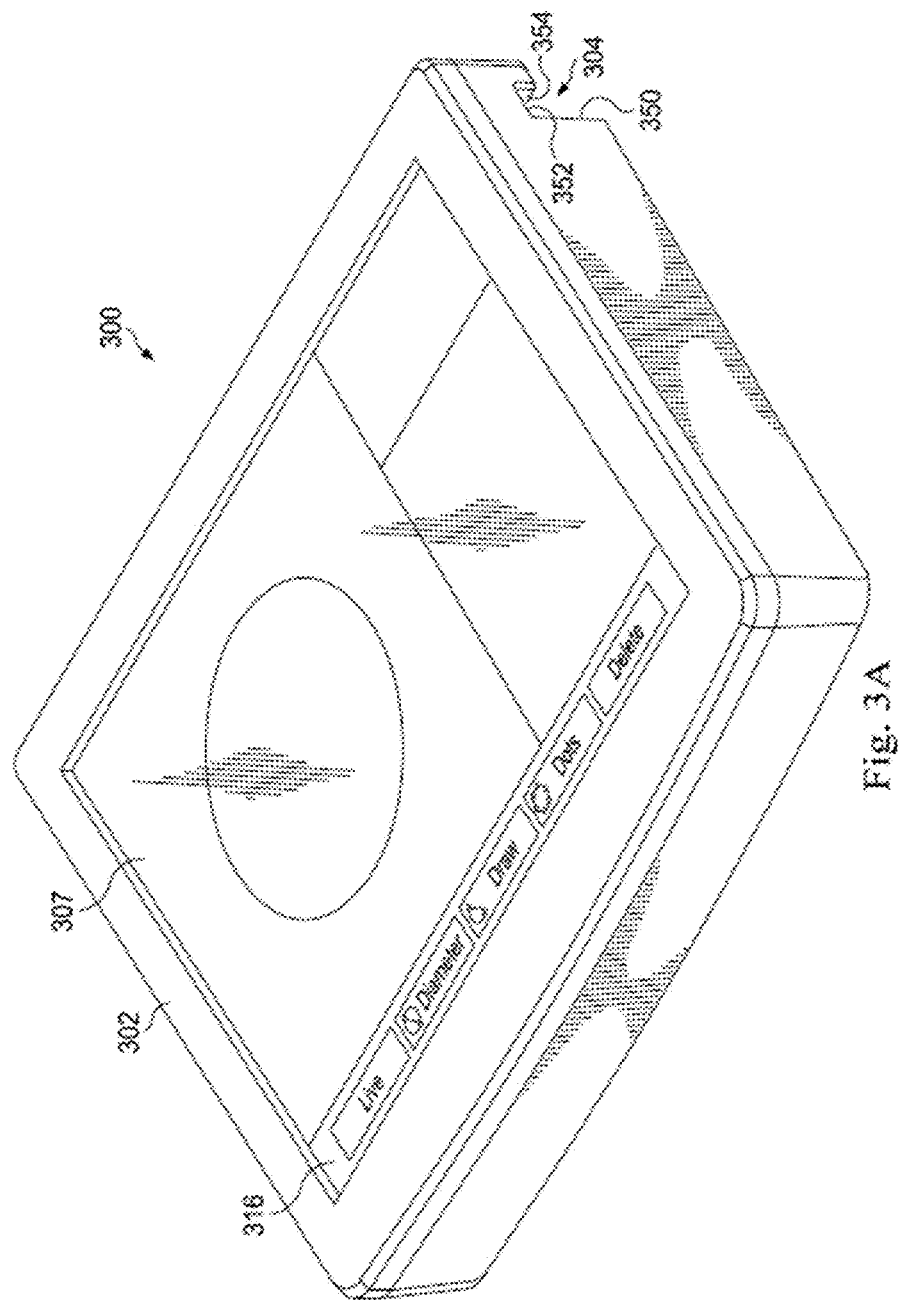
FIG. 3A is a diagrammatic perspective view of a bedside controller.
Figure 3B:
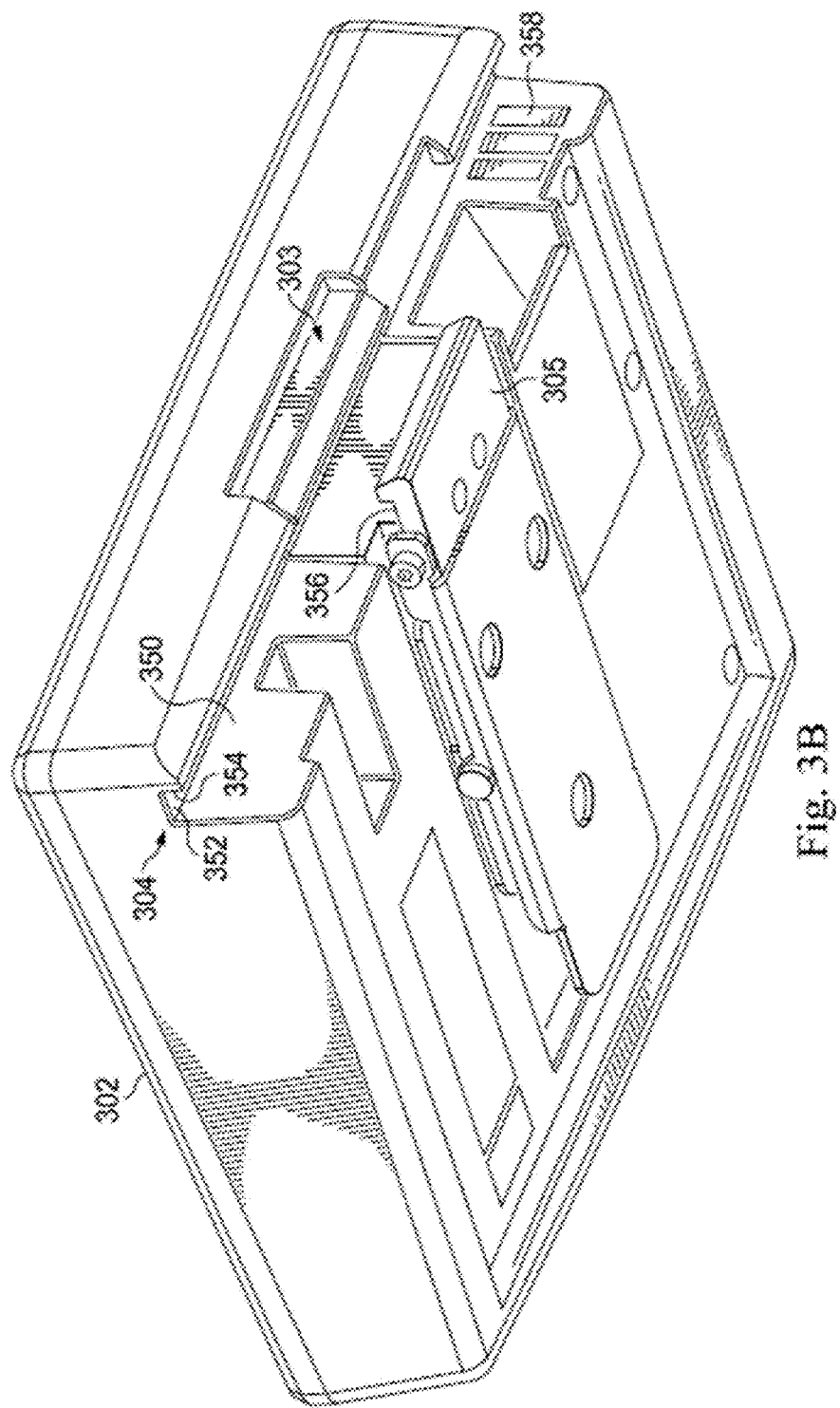
FIG. 3B is a diagrammatic rear perspective view of the bedside controller of FIG. 3A.
Figure 4:
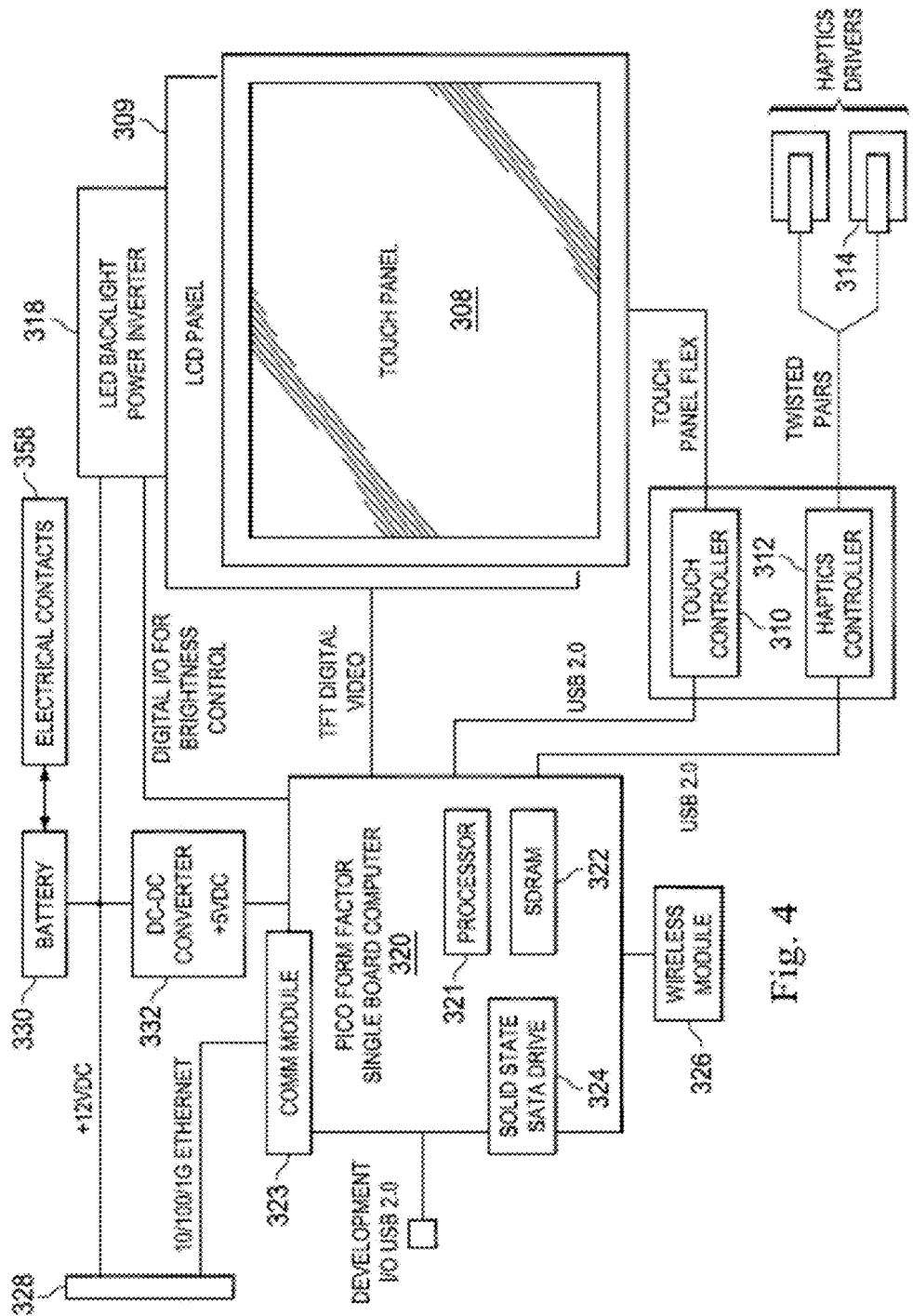
FIG. 4 is a functional block diagram of the bedside controller of FIGS. 3A-3C according to aspects of the present disclosure.

With reference now to FIGS. 3A, 3B, 3C and 4, FIG. 3A is a diagrammatic perspective view of a bedside controller 300, FIG. 3B is a diagrammatic rear perspective view of the bedside controller, FIG. 3C is a diagrammatic perspective view of the bedside controller mounted to a bed rail, and FIG. 4 is a functional block diagram of the bedside controller 300 according to aspects of the present disclosure. The bedside controller 300 is similar to the bedside controllers 102 and 202 in medical sensing systems 100 and 200, and is operable to, among other things, initiate a medical sensing or treatment procedure workflow, display real-time data (e.g., visual representations of pressure data) obtained during the procedure, and accept user touches on the visual representations of pressure data from a clinician. The bedside controller 300 generally improves system control available to a clinician working at a patient table. For instance, giving a clinician both workflow control and analysis capability within the sterile field reduces errors and improves workflow efficiency.

As show in FIG. 3A, the bedside controller 300 includes an integrally formed housing 302 that is easy to grasp and move around a catheter lab or other medical setting. In one embodiment, the integrally formed housing 302 may be seamlessly molded from materials such as thermoplastic or thermosetting plastic or moldable metal. In other embodiments, the integrally formed housing 302 may comprise a plurality of housing portions fixedly bonded in a substantially permanent manner to form an integral housing. The housing 302 is resistant to fluids, and, in one embodiment, may have a rating of IPX4 against fluid ingress as defined by the International Electrotechnical Commission (IEC) standard 60529. In other embodiments in which the housing 302 may be used in different environments, the hub may have a different fluid ingress rating. In the illustrated embodiment, the housing 302 is about 10.5 inches in width, about 8.25 inches in height, and has as thickness of about 2.75 inches. In alternative embodiments, the housing may have a different width, height, or thickness that is similarly conducive to portability.

As shown in FIG. 3B, the housing 302 further includes self-contained mounting structure 303 disposed on the housing. In the illustrated embodiment, the mounting structure is disposed near an outer edge of the housing. The mounting structure 303 allows the bedside controller 300 to be releasably mounted in a variety of places in and out of a catheter lab in a self-contained manner. That is, the bedside controller 300 may be directly secured to another object without the use of a separate external mount. In the illustrated embodiment, the mounting structure 303 includes a mounting channel 304 and a retaining clamp 305 that pivots over the mounting channel to secure a mounting platform therewithin. The mounting channel 304 is defined by a longer front wall 350, a top wall 352, and a shorter back wall 354, and the retaining clamp includes a slot 356 that extends through the clamp in a manner generally parallel to the mounting channel. The front wall 350 and the back wall 354 are generally perpendicular to a touch-sensitive display 307 in the housing 302, and the top wall 352 is generally parallel to the display 307. In the illustrated embodiment, the retaining clamp is spring-loaded and releasably exerts pressure on objects situated in the mounting channel. In alternative embodiments, the retaining clamp may be configured differently and exert force via mechanisms other than springs.

As shown in FIG. 3C, in operation, the bedside controller 300 may be releasably secured to a mounting platform, for example a bed rail 306, by pivoting the mounting clamp 305 to an open position, positioning the controller such that the rail extends through the length of the channel 304, and releasing the clamp such that it secures the rail within the channel. When the rail 306 is positioned in the mounting channel 304 and the clamp 305 is holding it therein, three surfaces of the rail are respectively engaged by the front wall 350, the top wall 352, and the back wall 354, and a fourth surface of the rail extends through the slot 356 in the clamp 305. In this manner, the mounting structure 303 may maintain the bedside controller 300 in a position generally parallel to a procedure table 350 associated with the bed rail 306, as shown in FIG. 3B. Described differently, the mounting structure 303 is a cantilevered mounting structure in that it secures one end of the controller to an object while the majority of the controller extends away from the object in an unsupported manner. Such a cantilevered position allows for a display of the controller to be both readable and at a comfortable input angle for an operator. Further, the self-contained mounting structure 303 allows the bedside controller 300 to be quickly released from the bed rail 306 and reattached to an IV pole, a cart on which a processing system is deployed, or other location in or out of the sterile field to allow for convenient workflow control and image analysis. In alternative embodiments the mounting structure 303 of the bedside controller may vary from the design illustrated in FIGS. 3A and 3B and include additional and/or different components to allow for self-contained mounting.

Embedded into the front of the housing 302 is the touch-sensitive display 307 that comprises both a touch panel 308 and a flat panel display 309. The touch panel 308 overlays the flat panel display 308 and accepts user input via human touch, stylus touch, or some other analogous input method. In other words, the touch-sensitive display 307 displays images and accepts user input on the same surface. In the current embodiment, the touch panel 308 is a resistive-type panel, but in alternative embodiments it may be a capacitive-type panel, projective-type panel, or some other suitable type of touch enabled input panel. Further, the touch panel 308 is operable to accept multiple inputs simultaneously (multitouch), for instance, to enable rotation of a three-dimensional rendering of a vessel along multiple axes. Additionally, the touch panel 308 is capable of receiving input when a sterile drape 301 is covering the bedside controller 300 and also when a user is gloved. The touch panel 308 is controlled by a touch controller 310 disposed within the housing 302. Further, when a clinician makes contact with the touch panel 308, the touch panel is operable to provide haptic feedback via a haptics controller 312 and haptics drivers 314. This haptic technology is operable to simulate a plurality of sensations on the touch panel 308 by varying the intensity and frequency of vibrations generated when a user contacts the touch panel. In some embodiments, the housing 302 may include a sheath configured to store a stylus therein. Thus, a clinician may remove the stylus from the sheath in the housing to make measurements on the bedside controller and store it when the measurements have been completed.

Beneath the touch panel 308 is the flat panel display 309 that presents a graphical user interface (GUI) 316 to a user. In the illustrated embodiment, the flat panel display 309 is a LCD display but in alternative embodiments, it may be a different type of display such an LED display or an AMO-LED display. In the illustrated embodiment, the flat panel display 309 is illuminated by a LED backlight power inverter 318. As mentioned above, the GUI 316 not only allows a clinician to control a medical sensing workflow, but also view and interact with pressure data obtained from a patient in the sterile field. A method of interacting with the GUI 316 to view and interact with the data will be discussed in greater detail in association with FIGS. 7-12.

The bedside controller 300 includes a single board processing platform 320 within the housing 302 that is operable to render the GUI 316 and process user touch input. In the illustrated embodiment, the processing platform has a pico form factor and includes integrated processing components such as a processor 321, system memory 322, graphics processing unit (GPU), communications module 323, and I/O bus controller. In some embodiments, the processor 321 may be a low power processor such as an Intel Atom® processor or an ARM-based processor, and the communications module 323 may be a 10/100/1 Gb Ethernet module. And, the I/O bus controller may be a Universal Serial Bus (USB) controller. The bedside controller 300 further includes a storage module 324 that is a non-transitory computer readable storage medium operable to store an operating system (i.e. software to render and control the GUI), data and/or visual representation manipulation software, medical sensing data and visual representations received from a processing system, and other medical sensing-related software. The processor 321 is configured to execute software and instructions stored on the storage module 324. In the illustrated embodiment, the storage module 324 is a solid state drive (SSD) hard drive communicatively coupled to the processing platform 320 via a SATA connection, but, in alternative embodiments, it may be any other type of non-volatile or temporary storage module. The bedside controller 300 further includes a wireless communications module 326 communicatively coupled to the processing platform 320. In some embodiments, the wireless communications module is a IEEE 802.11 Wi-Fi module, but in other may be a Ultra Wide-Band (UWB) wireless module, a wireless FireWire module, a wireless USB module, a Bluetooth module, or another high-speed wireless networking module.

In the illustrated embodiment, the bedside controller 300 is powered via both a wired 12VDC power-over-Ethernet (PoE) connection 328 and a battery 330 disposed within the housing 302. In one embodiment, the battery 330 may be sealed within the integrally formed housing 302 and may be recharged through electrical contacts disposed on the exterior of the housing and electrically coupled to the battery. As shown in the embodiment of FIG. 3B, the front wall 350 may include one or more electrical contacts 358 through which the battery 330 may be charged when the controller is mounted to objects with compatible charging structure. In other embodiments, the housing 302 may include a battery compartment with a removable cover to permit battery replacement. Such a battery compartment cover may be resistant to fluid ingress (e.g., with an IPX4 rating). The beside controller 300 may be coupled to a processing system in the catheter lab via the PoE connection 328, over which it receives medical sensing images that have been captured from the patient and rendered on the processing system. In operation, when the bedside controller is coupled to the PoE connection 328, it receives power and communications over the same physical wire. When the bedside controller 300 is disconnected from the PoE connection 328, it runs on battery power and receives data wirelessly via the wireless communications module 326. When used wirelessly in a catheter lab, the beside controller may directly communicate with a processing system (i.e. in an ad-hoc wireless mode), or, alternatively, it may communicate with a wireless network that serves a plurality of wireless devices. In alternative embodiments, the bedside controller 300 may receive power and data through different wired connections, or receive data communications through a wired data connection and power from the battery 330, or receive data communications through the wireless module 326 and power from a wired electrical connection. In some embodiments, the bedside controller 300 may be used in a semi-wireless configuration, in which the battery 330 provides backup power to the controller when the controller is temporarily disconnected from a wired power source. For example, if at the beginning of a procedure, the bedside controller 300 is connected to a PoE connection (or other type of wired connection) and during the procedure the controller must be disconnected from the PoE connection to allow for a cabling adjustment, the battery 330 may keep the controller alive until a PoE connection can be re-established. In this manner, a full power-off and reboot of the controller 300 is avoided during a procedure. As shown in FIG. 4, a DC-DC power converter 332 converts input voltage to a voltage usable by the processing platform 320.

It is understood that although the bedside controller 300 in the illustrated embodiments of FIGS. 3 and 4 includes specific components described herein, the bedside controller may include any number of additional components, for example a charge regulator interposed between the electrical contacts and the battery, and may be configured in any number of alternative arrangements in alternative embodiments.

Figure 5:
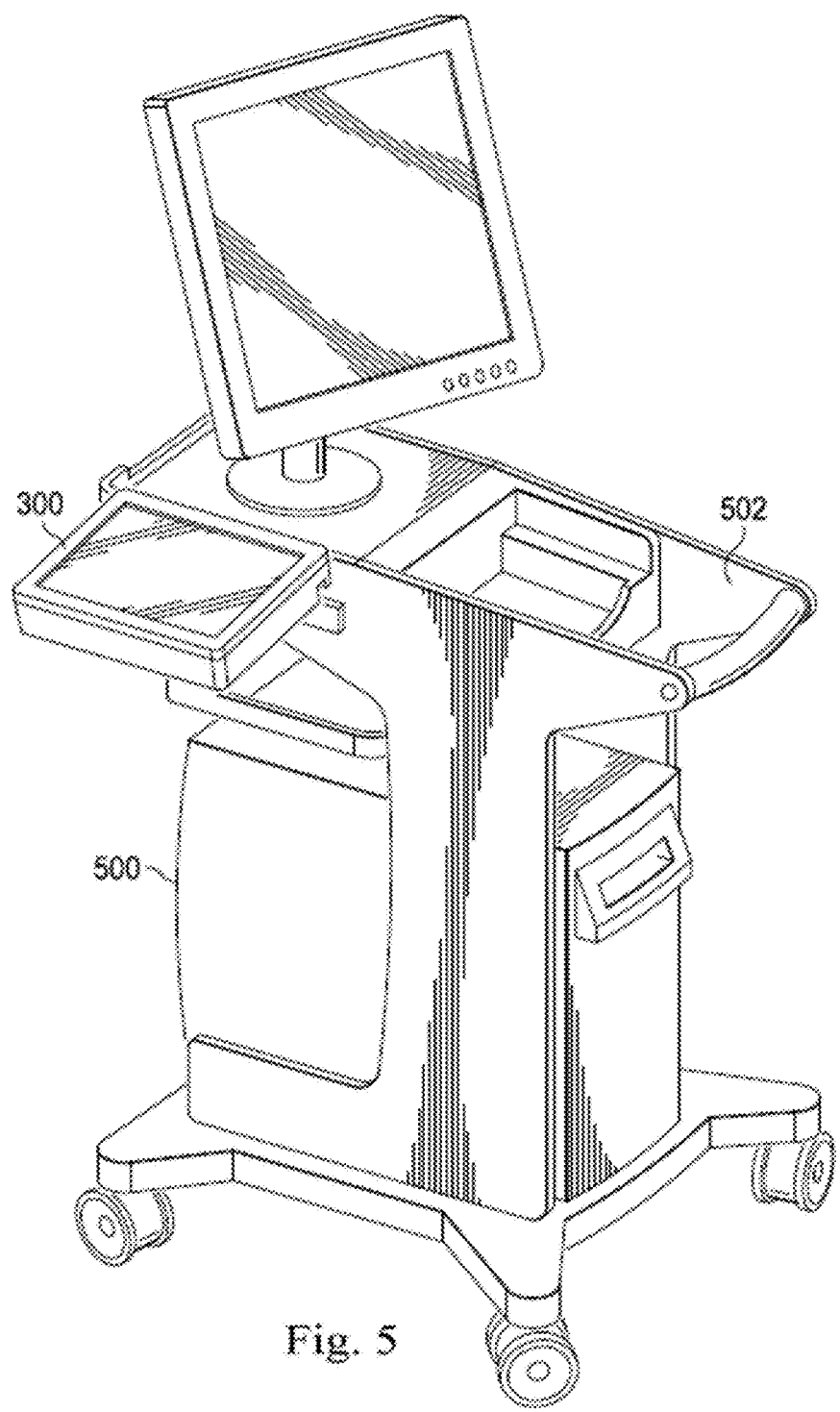
FIG. 5 is a diagrammatic perspective view of a mobile processing system with the bedside controller of FIGS. 3A-3C attached thereto.
Figure 6:
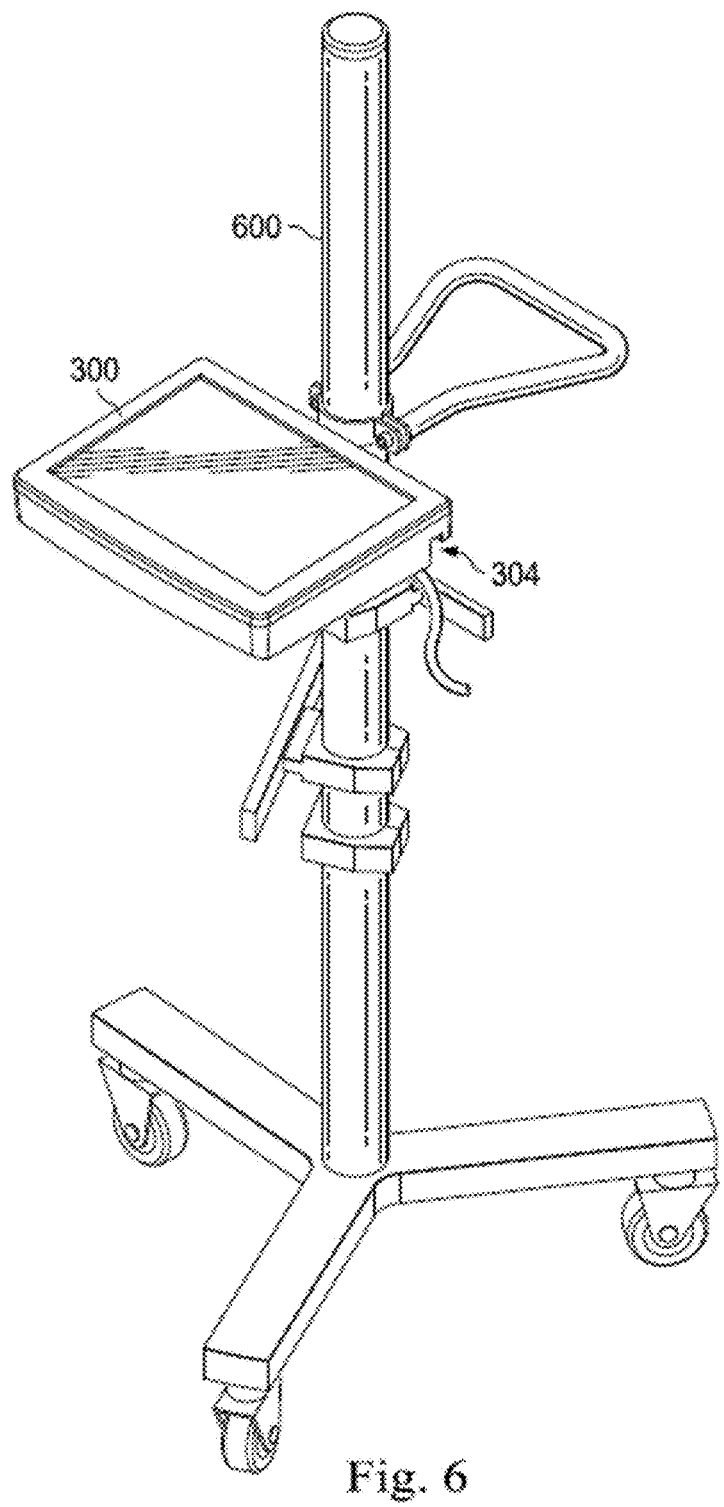
FIG. 6 is a diagrammatic perspective view of the bedside controller of FIGS. 3A-3C releasably mounted on an IV pole.

With reference now to FIGS. 5 and 6, illustrated are examples of locations in which the bedside controller 300 may be mounted. FIG. 5 is a diagrammatic perspective view of a mobile processing system 500. The processing system 500 is disposed on a cart 502 that enables the processing system to be easily moved between different locations such as different catheter labs. As shown in FIG. 5, the bedside controller 300 is mounted to the cart 502 so that it may be transported to catheter labs with the processing system. The bedside controller 300 is releasably secured to the cart via the self-contained mounting structure 303 that is built into the housing 302. Further, in some embodiments, the cart 502 may include a dock for the bedside controller 300 such that when the controller is docked on the cart its battery is recharged through the electrical contacts 358 disposed on the housing 302. As shown in FIG. 6, the bedside controller 300 may also releasably attach to an IV pole 600 via the self-contained mounting structure 303. When so attached, the bedside controller 300 may be rolled next to a patient in the sterile field and thus within reach of a clinician who may operate the controller with a single hand.

Figure 7:
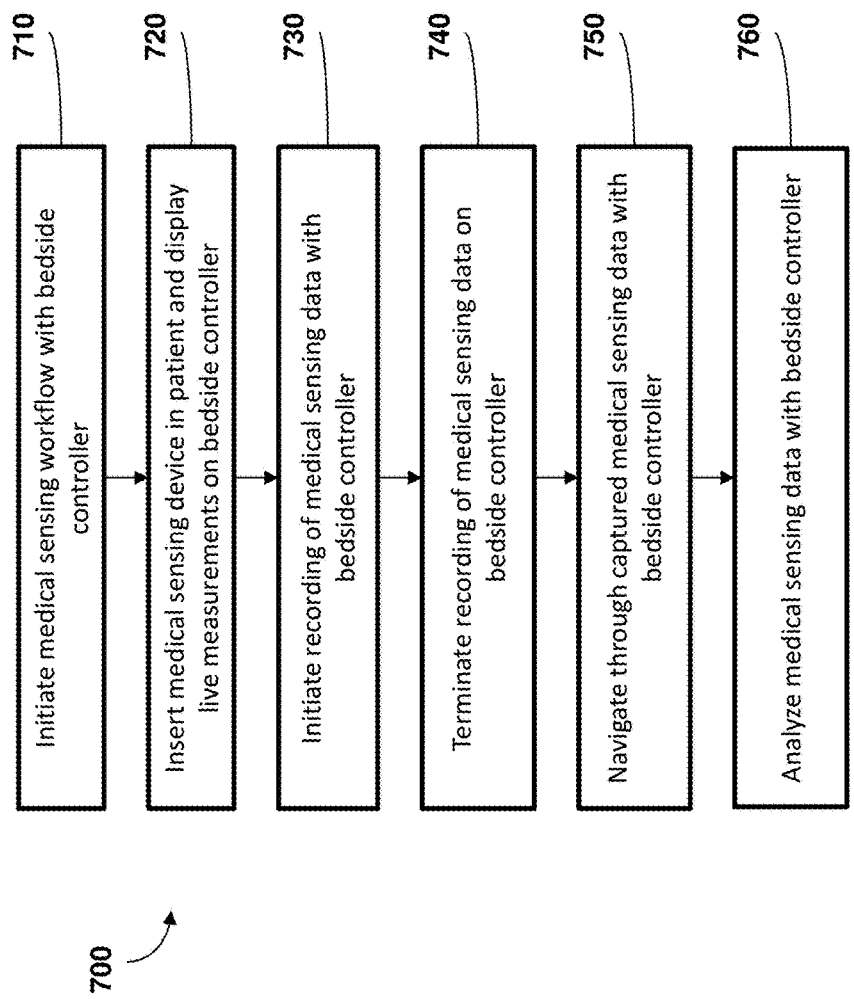
FIG. 7 is a flowchart illustrating a method of conducting a medical sensing workflow with a bedside controller according to various aspects of the present disclosure.

FIG. 7 is a flowchart illustrating a method 700 of conducting a medical sensing workflow with the bedside controller 300 of FIGS. 3A-4 according to various aspects of the present disclosure. The method 700 will be described in the context of a pressure-sensing procedure, such as an iFR procedure, but may equally apply to any number of medical sensing or treatment procedures, such as an FFR procedure, an IVUS procedure, OCT procedure, a FLIVUS procedure, an ICE procedure, etc. The method 700 can be better understood with reference to the FIGS. 8-16. The method 700 begins at block 710 where a medical sensing workflow is initiated with the bedside controller 300. Using an iFR procedure as an example, a clinician in the sterile field and adjacent a patient may select the "iFR" option out of a plurality of modes (e.g., FFR, iFR, CFR, etc.) on the bedside controller's GUI to begin the iFR workflow. Next, in block 720, after a pressure-sensing intravascular device, such as a catheter or guidewire, has been inserted into the patient, the clinician may select a 'Live' option on the bedside controller's GUI to receive live pressure measurements from the intravascular device. In some embodiments, the clinician may guide the intravascular device within the patient to a desired position using the real-time pressure measurements. In typical embodiments, a processing system may collect raw pressure data from the intravascular device and process the data to render visual representations of the obtained pressure data. The bedside controller retrieves the visual representations from the processing system and displays them to a user in real-time. Then, in block 730, after the pressure sensing intravascular device has been appropriately positioned in the patient, the clinician selects a 'Record' option on the bedside controller GUI. Pressure measurements can be collected during one or more of the following procedures: an FFR "spot" measurement where the pressure sensor stays in one place while hyperemia is induced; an FFR pullback in which an elongated period of hyperemia is induced and the sensor is pulled back to the ostium; an iFR "spot" measurement that is similar to the FFR spot measurement but without hyperemia; and an iFR pullback which is that the FFR pullback but without hyperemia. The processing system responds to the record command and begins rendering and storing the pressure measurements and visual representations generated from the pressure measurements. The visual representations can include numerical, graphical, textual, and/or other suitable visualizations. The method 700 proceeds to block 740 where, after the pressure measurement collection procedure has been completed, the clinician terminates the recording of pressure measurements via the bedside controller's GUI. Then, in block 750, the clinician at the bedside recalls and navigates through the pressure measurements or corresponding visual representations on the bedside controller. Specifically, the bedside controller may present pressure measurements or visual representations of the obtained pressure data on the bedside controller and the clinician may navigate through them using gestures on the bedside controller's touch panel. Finally, in block 760, the clinician analyzes the obtained pressure data or visual representations of the obtained pressure data, directly on the bedside controller. For example, the user of the bedside controller interacts with the obtained pressure data or visual representations through a series of presses, moves and releases using a finger or stylus on the controller's touch-sensitive display. These actions are interpreted by the bedside controller's internal processor. In some embodiments, the obtained pressure data and/or visual representations can be modified in response to the user touch inputs. For example, a user touch input on the bedside controller can select a specific point a pressure waveform that corresponds to a specific time at which pressure measurements were obtained. In response to the user touch input, pressure data obtained at the specific time can be displayed proximate the specific point on the pressure waveform on the bedside controller.

Figure 8:
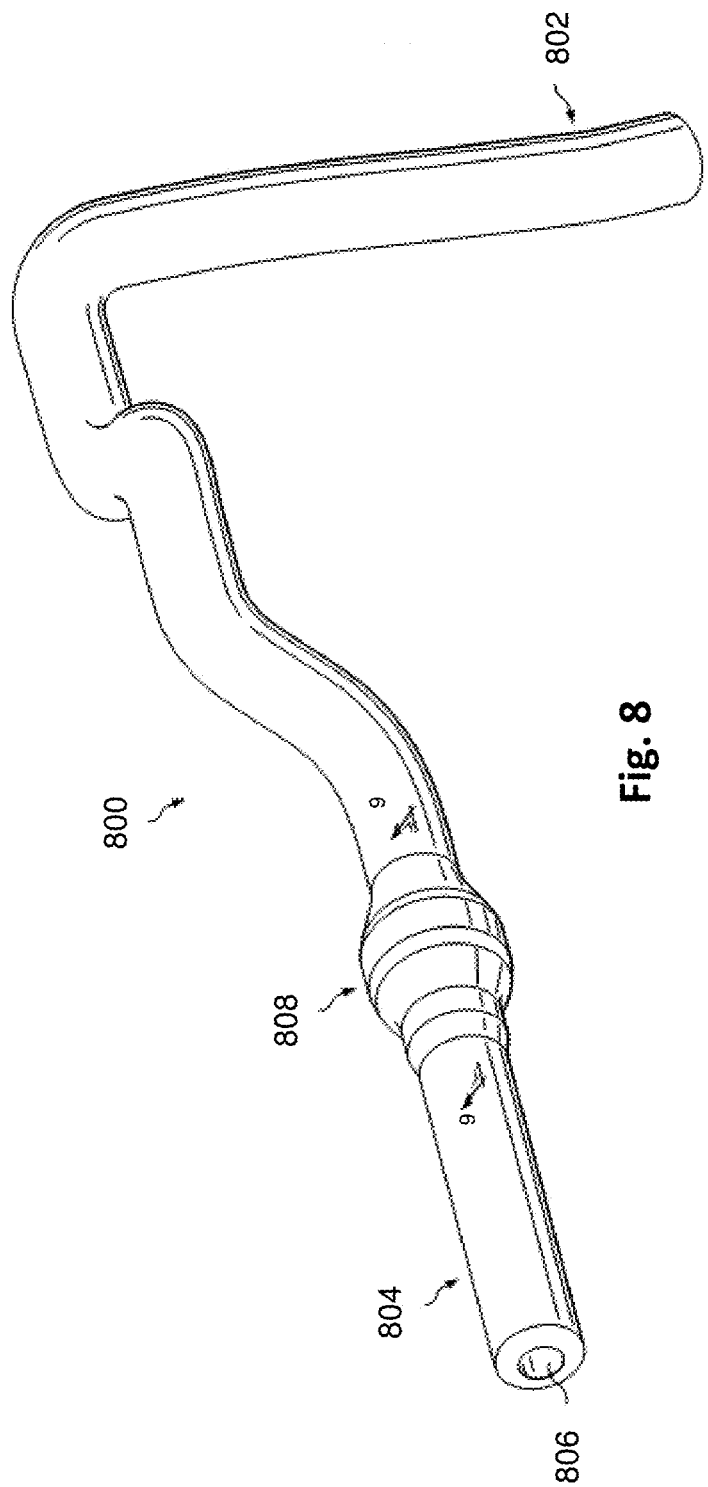
FIG. 8 shows a diagrammatic perspective view of a vessel having a stenosis according to an embodiment of the present disclosure.
Figure 9:
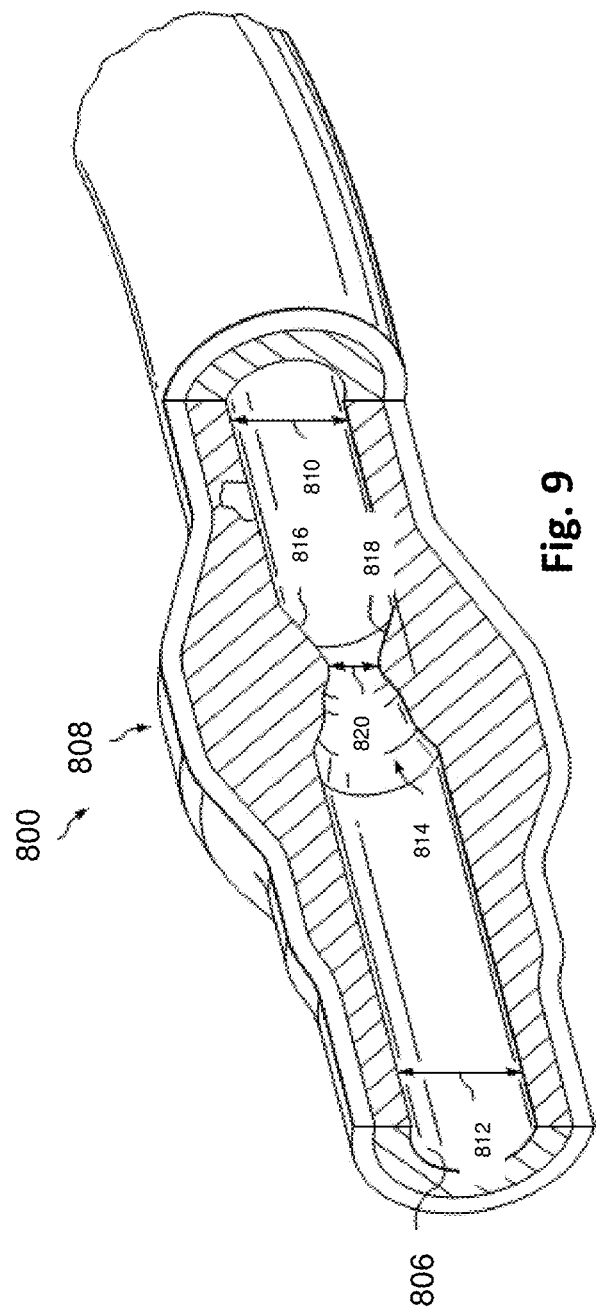
FIG. 9 shows a diagrammatic, partial cross-sectional perspective view of a portion of the vessel of FIG. 8 taken along section line 9-9 of FIG. 8.

Referring to FIGS. 8 and 9, shown therein is a vessel 800 having a stenosis according to an embodiment of the present disclosure. In that regard, FIG. 8 is a diagrammatic perspective view of the vessel 800, while FIG. 9 is a partial cross-sectional perspective view of a portion of the vessel 800 taken along section line 9-9 of FIG. 1. Referring more specifically to FIG. 8, the vessel 800 includes a proximal portion 802 and a distal portion 804. A lumen 806 extends along the length of the vessel 800 between the proximal portion 802 and the distal portion 804. In that regard, the lumen 806 is configured to allow the flow of fluid through the vessel. In some instances, the vessel 800 is a blood vessel. In some particular instances, the vessel 800 is a coronary artery. In such instances, the lumen 806 is configured to facilitate the flow of blood through the vessel 800.

As shown, the vessel 800 includes a stenosis 808 between the proximal portion 802 and the distal portion 804. Stenosis 808 is generally representative of any blockage or other structural arrangement that results in a restriction to the flow of fluid through the lumen 806 of the vessel 800. Embodiments of the present disclosure are suitable for use in a wide variety of vascular applications, including without limitation coronary, peripheral (including but not limited to lower limb, carotid, and neurovascular), renal, and/or venous. Where the vessel 800 is a blood vessel, the stenosis 808 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 9, the lumen 806 of the vessel 800 has a diameter 810 proximal of the stenosis 808 and a diameter 812 distal of the stenosis. In some instances, the diameters 810 and 812 are substantially equal to one another. In that regard, the diameters 810 and 812 are intended to represent healthy portions, or at least healthier portions, of the lumen 806 in comparison to stenosis 808. Accordingly, these healthier portions of the lumen 806 are illustrated as having a substantially constant cylindrical profile and, as a result, the height or width of the lumen has been referred to as a diameter. However, it is understood that in many instances these portions of the lumen 806 will also have plaque buildup, a non-symmetric profile, and/or other irregularities, but to a lesser extent than stenosis 808 and, therefore, will not have a cylindrical profile. In such instances, the diameters 810 and 812 are understood to be representative of a relative size or cross-sectional area of the lumen and do not imply a circular cross-sectional profile.

As shown in FIG. 9, stenosis 808 includes plaque buildup 814 that narrows the lumen 806 of the vessel 800. In some instances, the plaque buildup 814 does not have a uniform or symmetrical profile, making angiographic evaluation of such a stenosis unreliable. In the illustrated embodiment, the plaque buildup 814 includes an upper portion 816 and an opposing lower portion 818. In that regard, the lower portion 818 has an increased thickness relative to the upper portion 816 that results in a non-symmetrical and non-uniform profile relative to the portions of the lumen proximal and distal of the stenosis 808. As shown, the plaque buildup 814 decreases the available space for fluid to flow through the lumen 806. In particular, the cross-sectional area of the lumen 806 is decreased by the plaque buildup 814. At the narrowest point between the upper and lower portions 816, 818 the lumen 806 has a height 820, which is representative of a reduced size or cross-sectional area relative to the diameters 810 and 812 proximal and distal of the stenosis 808. Note that the stenosis 808, including plaque buildup 814 is exemplary in nature and should be considered limiting in any way. In that regard, it is understood that the stenosis 808 has other shapes and/or compositions that limit the flow of fluid through the lumen 806 in other instances. While the vessel 800 is illustrated in FIGS. 8 and 9 as having a single stenosis 808 and the description of the embodiments below is primarily made in the context of a single stenosis, it is nevertheless understood that the devices, systems, and methods described herein have similar application for a vessel having multiple stenosis regions.

Figure 10:
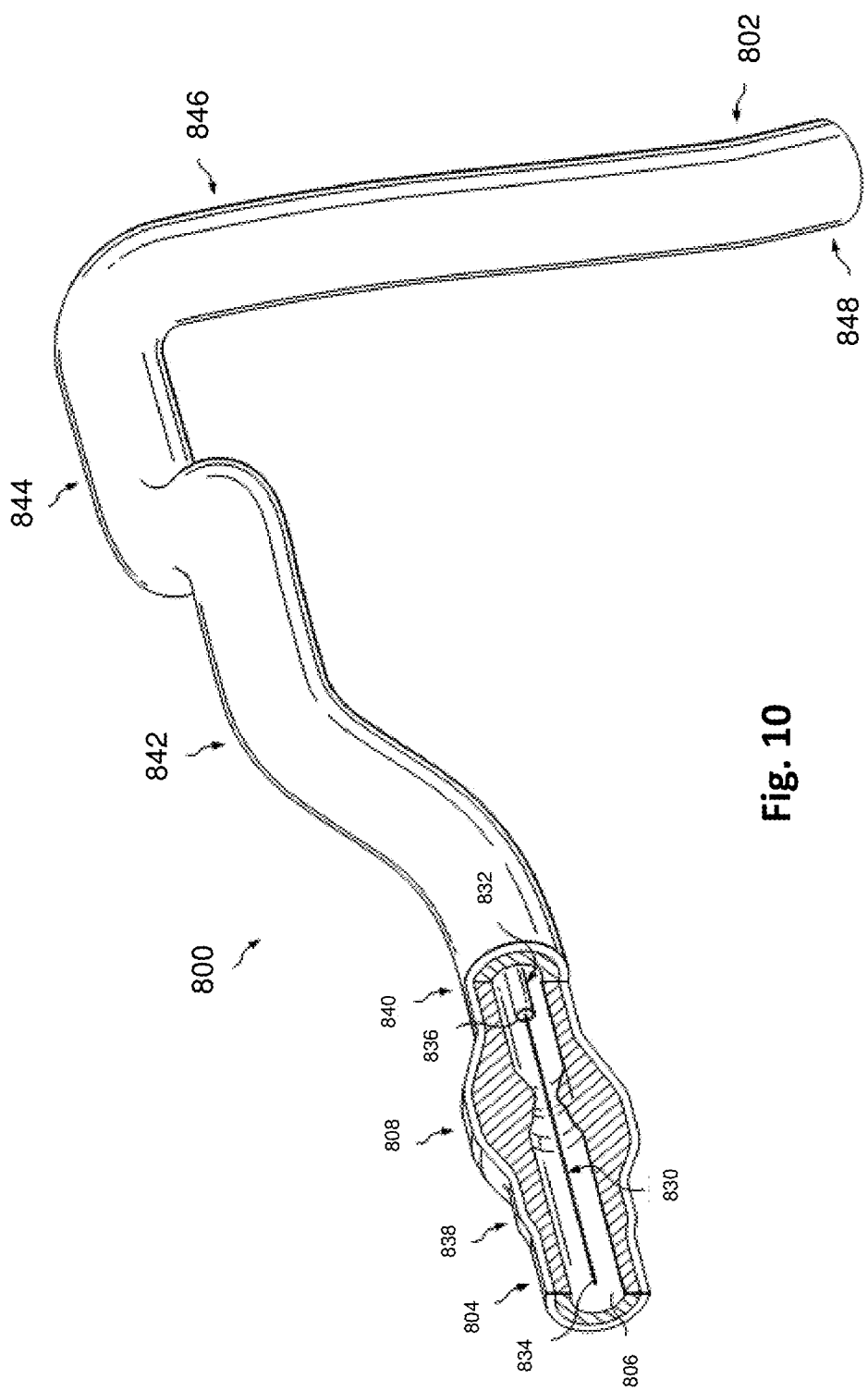
FIG. 10 shows a diagrammatic, partial cross-sectional perspective view of the vessel of FIGS. 8 and 9 with instruments positioned therein according to an embodiment of the present disclosure.

Referring now to FIG. 10, the vessel 800 is shown with instruments 830 and 832 positioned therein according to an embodiment of the present disclosure. In general, instruments 830 and 832 may be any form of device, instrument, or probe sized and shaped to be positioned within a vessel. The instruments 830 and 832 can be implemented in the medical sensing system 100 (FIG. 1) as medical sensing devices 108 and 110. In the illustrated embodiment, instrument 830 is generally representative of a guide wire, while instrument 832 is generally representative of a catheter. In that regard, instrument 830 extends through a central lumen of instrument 832. However, in other embodiments, the instruments 830 and 832 take other forms. In that regard, the instruments 830 and 832 are of similar form in some embodiments. For example, in some instances, both instruments 830 and 832 are guide wires. In other instances, both instruments 830 and 832 are catheters. On the other hand, the instruments 830 and 832 are of different form in some embodiments, such as the illustrated embodiment, where one of the instruments is a catheter and the other is a guide wire. Further, in some instances, the instruments 830 and 832 are disposed coaxial with one another, as shown in the illustrated embodiment of FIG. 10. In other instances, one of the instruments extends through an off-center lumen of the other instrument. In yet other instances, the instruments 830 and 832 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 830 and 832 a single instrument is utilized. In some embodiments, the single instrument incorporates aspects of the functionalities (e.g., data acquisition) of both instruments 830 and 832.

Instrument 830 is configured to obtain diagnostic information about the vessel 800. In that regard, the instrument 830 includes one or more sensors, transducers, and/or other monitoring elements configured to obtain the diagnostic information about the vessel. The diagnostic information includes one or more of pressure, flow (velocity and/or volume), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 830 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 834 of the instrument 830 in some instances. In some instances, at least one of the one or more sensors, transducers, and/or other monitoring elements is positioned at the distal tip of the instrument 830.

The instrument 830 includes at least one element configured to monitor pressure within the vessel 800. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 830 is sized such that it can be positioned through the stenosis 808 without significantly impacting fluid flow across the stenosis, which would impact the distal pressure reading. Accordingly, in some instances the instrument 830 has an outer diameter of 0.018" or less. In some embodiments, the instrument 830 has an outer diameter of 0.014" or less.

Instrument 832 is also configured to obtain diagnostic information about the vessel 100. In some instances, instrument 832 is configured to obtain the same diagnostic information as instrument 830. In other instances, instrument 832 is configured to obtain different diagnostic information than instrument 830, which may include additional diagnostic information, less diagnostic information, and/or alternative diagnostic information. The diagnostic information obtained by instrument 832 includes one or more of pressure, flow (velocity and/or volume), images (including images obtained using ultrasound (e.g., IVUS), OCT, thermal, and/or other imaging techniques), temperature, and/or combinations thereof. Instrument 832 includes one or more sensors, transducers, and/or other monitoring elements configured to obtain this diagnostic information. In that regard, the one or more sensors, transducers, and/or other monitoring elements are positioned adjacent a distal portion of the instrument 832 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 836 of the instrument 832 in some instances. In some instances, at least one of the one or more sensors, transducers, and/or other monitoring elements is positioned at the distal tip of the instrument 832.

Similar to instrument 830, instrument 832 also includes at least one element configured to monitor pressure within the vessel 800. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 832 in some instances.

In accordance with aspects of the present disclosure, at least one of the instruments 830 and 832 is configured to monitor a pressure within the vessel 800 distal of the stenosis 808 and at least one of the instruments 830 and 832 is configured to monitor a pressure within the vessel proximal of the stenosis. In that regard, the instruments 830, 832 are sized and shaped to allow positioning of the at least one element configured to monitor pressure within the vessel 800 to be positioned proximal and/or distal of the stenosis 808 as necessary based on the configuration of the devices. In that regard, FIG. 10 illustrates a position 838 suitable for measuring pressure distal of the stenosis 808. In that regard, the position 838 is less than 5 cm, less than 3 cm, less than 2 cm, less than 1 cm, less than 5 mm, and/or less than 2.5 mm from the distal end of the stenosis 808 (as shown in FIG. 9) in some instances. FIG. 10 also illustrates a plurality of suitable positions for measuring pressure proximal of the stenosis 808. In that regard, positions 840, 842, 844, 846, and 848 each represent a position that is suitable for monitoring the pressure proximal of the stenosis in some instances. In that regard, the positions 840, 842, 844, 846, and 848 are positioned at varying distances from the proximal end of the stenosis 808 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 830 and 832 is configured to monitor pressure within the vessel 800 while being moved through the lumen 806. In some instances, instrument 830 is configured to be moved through the lumen 806 and across the stenosis 808. In that regard, the instrument 830 is positioned distal of the stenosis 808 and moved proximally (i.e., pulled back) across the stenosis to a position proximal of the stenosis in some instances. In other instances, the instrument 830 is positioned proximal of the stenosis 808 and moved distally across the stenosis to a position distal of the stenosis. Movement of the instrument 830, either proximally or distally, is controlled manually by medical personnel (e.g., hand of a surgeon) in some embodiments. In other embodiments, movement of the instrument 830, either proximally or distally, is controlled automatically by a movement control device (e.g., a pullback device, such as the Trak Back® II Device available from Volcano Corporation). In that regard, the movement control device controls the movement of the instrument 830 at a selectable and known speed (e.g., 2.0 mm/s, 1.0 mm/s, 0.5 mm/s, 0.2 mm/s, etc.) in some instances. Movement of the instrument 830 through the vessel is continuous for each pullback or push through, in some instances. In other instances, the instrument 830 is moved step-wise through the vessel (i.e., repeatedly moved a fixed amount of distance and/or a fixed amount of time). Some aspects of the visual depictions discussed below are particularly suited for embodiments where at least one of the instruments 830 and 832 is moved through the lumen 806. Further, in some particular instances, aspects of the visual depictions discussed below are particularly suited for embodiments where a single instrument is moved through the lumen 806, with or without the presence of a second instrument.

In some instances, use of a single instrument has a benefit in that it avoids issues associated with variations in pressure measurements of one instrument relative to another over time, which is commonly referred to as drift. In that regard, a major source of drift in traditional Fractional Flow Reserve (FFR) measurements is divergence in the pressure reading of a guide wire relative to the pressure reading of a guide catheter. In that regard, because FFR is calculated as the ratio of the pressure measurement obtained by the guide wire to the pressure measurement obtained by the catheter, this divergence has an impact on the resulting FFR value. In contrast, where a single instrument is utilized to obtain pressure measurements as it is moved through the vessel, drift is negligible or non-existent. For example, in some instances, the single instrument is utilized to obtain relative changes in pressures as it is moved through the vessel such that the time period between pressure measurements is short enough to prevent any impact from any changes in pressure sensitivity of the instrument (e.g., less than 500 ms, less than 100 ms, less than 50 ms, less than 10 ms, less than 5 ms, less than 1 ms, or otherwise).

Figure 11:
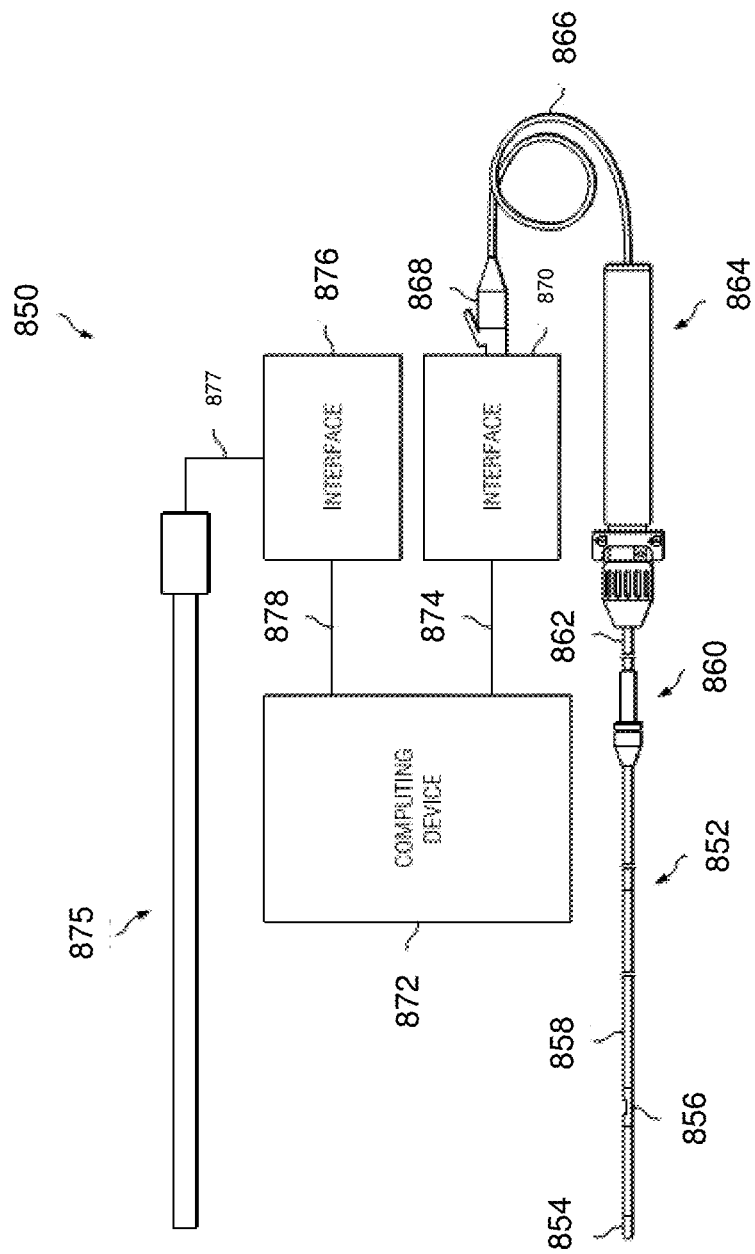
FIG. 11 shows a diagrammatic, schematic view of a system according to an embodiment of the present disclosure.

Referring now to FIG. 11, shown therein is a system 850 according to an embodiment of the present disclosure. In that regard, FIG. 11 is a diagrammatic, schematic view of the system 850. In some embodiments, the system 850 can be implemented as the medical sensing system 100 (FIG. 1). In some embodiments, one or more components of the medical sensing system 100 can be additionally implemented in the system 850, such as a bedside controller having a touch-sensitive display. As shown, the system 850 includes an instrument 852. In that regard, in some instances instrument 852 is suitable for use as at least one of instruments 830 and 832 (FIGS. 8-10) and/or medical sensing devices 108 and 110 (FIG. 1), discussed above. Accordingly, in some instances the instrument 852 includes features similar to those discussed above with respect to instruments 830 and 832 in some instances. In the illustrated embodiment, the instrument 852 is a guide wire having a distal portion 854 and a housing 856 positioned adjacent the distal portion. In that regard, the housing 856 is spaced approximately 3 cm from a distal tip of the instrument 852. The housing 856 is configured to house one or more sensors, transducers, and/or other monitoring elements configured to obtain the diagnostic information about the vessel. In the illustrated embodiment, the housing 856 contains at least a pressure sensor configured to monitor a pressure within a lumen in which the instrument 852 is positioned. A shaft 858 extends proximally from the housing 856. A torque device 860 is positioned over and coupled to a proximal portion of the shaft 858. A proximal end portion 862 of the instrument 852 is coupled to a connector 864. A cable 866 extends from connector 864 to a connector 868. In some instances, connector 868 is configured to be plugged into an interface 870. In that regard, interface 870 is a patient interface module (PIM) in some instances. The interface 870 can be implemented as the PIM 112 (FIG. 1). In some instances, the cable 866 is replaced with a wireless connection. In that regard, it is understood that various communication pathways between the instrument 852 and the interface 870 may be utilized, including physical connections (including electrical, optical, and/or fluid connections), wireless connections, and/or combinations thereof.

The interface 870 is communicatively coupled to a computing device 872 via a connection 874. Computing device 872 is generally representative of any device suitable for performing the processing and analysis techniques discussed within the present disclosure. In some embodiments, the computing device 872 includes a processor, random access memory, and a storage medium. In that regard, in some particular instances the computing device 872 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 872 is the bedside controller. For example, the processing steps described herein can be performed by one or more processing components of the bedside controller, such as the processing platform 320 (FIG. 4). In some instances, the computing device 872 is a console device. In some particular instances, the computing device 872 is similar to the s5™ Imaging System or the s5i™ Imaging System, each available from Volcano Corporation. In some instances, the computing device 872 is portable (e.g., handheld, on a rolling cart, etc.). Further, it is understood that in some instances the computing device 872 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 864, cable 866, connector 868, interface 870, and connection 874 facilitate communication between the one or more sensors, transducers, and/or other monitoring elements of the instrument 852 and the computing device 872. However, this communication pathway is exemplary in nature and should not be considered limiting in any way. In that regard, it is understood that any communication pathway between the instrument 852 and the computing device 872 may be utilized, including physical connections (including electrical, optical, and/or fluid connections), wireless connections, and/or combinations thereof. In that regard, it is understood that the connection 874 is wireless in some instances. In some instances, the connection 874 includes a communication link over a network (e.g., intranet, internet, telecommunications network, and/or other network). In that regard, it is understood that the computing device 872 is positioned remote from an operating area where the instrument 152 is being used in some instances. Having the connection 874 include a connection over a network can facilitate communication between the instrument 852 and the remote computing device 872 regardless of whether the computing device is in an adjacent room, an adjacent building, or in a different state/country. Further, it is understood that the communication pathway between the instrument 852 and the computing device 872 is a secure connection in some instances. Further still, it is understood that, in some instances, the data communicated over one or more portions of the communication pathway between the instrument 852 and the computing device 872 is encrypted.

The system 850 also includes an instrument 875. In that regard, in some instances instrument 875 is suitable for use as at least one of instruments 130 and 132 (FIGS. 8-10) and/or medical sensing devices 108 and 110 (FIG. 1), discussed above. Accordingly, in some instances the instrument 875 includes features similar to those discussed above with respect to instruments 130 and 132 in some instances. In the illustrated embodiment, the instrument 875 is a catheter-type device. In that regard, the instrument 875 includes one or more sensors, transducers, and/or other monitoring elements adjacent a distal portion of the instrument configured to obtain the diagnostic information about the vessel. In the illustrated embodiment, the instrument 875 includes a pressure sensor configured to monitor a pressure within a lumen in which the instrument 875 is positioned. The instrument 875 is in communication with an interface 876 via connection 877. In some instances, interface 876 is a hemodynamic monitoring system or other control device, such as Siemens AXIOM Sensis, Mennen Horizon XVu, and Philips Xper IM Physiomonitoring 5. In one particular embodiment, instrument 875 is a pressure-sensing catheter that includes fluid column extending along its length. In such an embodiment, interface 876 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 876. In other instances, the pressure sensor is a separate component positioned between the instrument 875 and the interface 876. The interface 876 is communicatively coupled to the computing device 872 via a connection 878.

Similar to the connections between instrument 852 and the computing device 872, interface 876 and connections 877 and 878 facilitate communication between the one or more sensors, transducers, and/or other monitoring elements of the instrument 875 and the computing device 872. However, this communication pathway is exemplary in nature and should not be considered limiting in any way. In that regard, it is understood that any communication pathway between the instrument 875 and the computing device 872 may be utilized, including physical connections (including electrical, optical, and/or fluid connections), wireless connections, and/or combinations thereof. In that regard, it is understood that the connection 878 is wireless in some instances. In some instances, the connection 878 includes a communication link over a network (e.g., intranet, internet, telecommunications network, and/or other network). In that regard, it is understood that the computing device 872 is positioned remote from an operating area where the instrument 875 is being used in some instances. Having the connection 878 include a connection over a network can facilitate communication between the instrument 875 and the remote computing device 872 regardless of whether the computing device is in an adjacent room, an adjacent building, or in a different state/country. Further, it is understood that the communication pathway between the instrument 875 and the computing device 872 is a secure connection in some instances. Further still, it is understood that, in some instances, the data communicated over one or more portions of the communication pathway between the instrument 875 and the computing device 872 is encrypted.

It is understood that one or more components of the system 850 are not included, are implemented in a different arrangement/order, and/or are replaced with an alternative device/mechanism in other embodiments of the present disclosure. For example, in some instances, the system 850 does not include interface 870 and/or interface 876. In such instances, the connector 868 (or other similar connector in communication with instrument 852 or instrument 875) may plug into a port associated with computing device 872. Alternatively, the instruments 852, 875 may communicate wirelessly with the computing device 872. Generally speaking, the communication pathway between either or both of the instruments 852, 875 and the computing device 872 may have no intermediate nodes (i.e., a direct connection), one intermediate node between the instrument and the computing device, or a plurality of intermediate nodes between the instrument and the computing device. The system 850 can additionally include a bedside controller, such as the bedside controller of medical sensing system 100 (FIG. 1). The bedside controller may be utilized by a clinician to control a instruments 852 and 875 to acquire pressure data during a procedure, watch real-time medical pressure measurements (e.g., visual representations of pressure data, such as pressure waveforms, numerical values, etc.), and interact with the obtained medical sensing data using the bedside controller. In that regard, the bedside controller can be communicatively coupled to the computing device 872, the interfaces 870 and 876, and/or the instruments 864 and 875.

Figure 12:
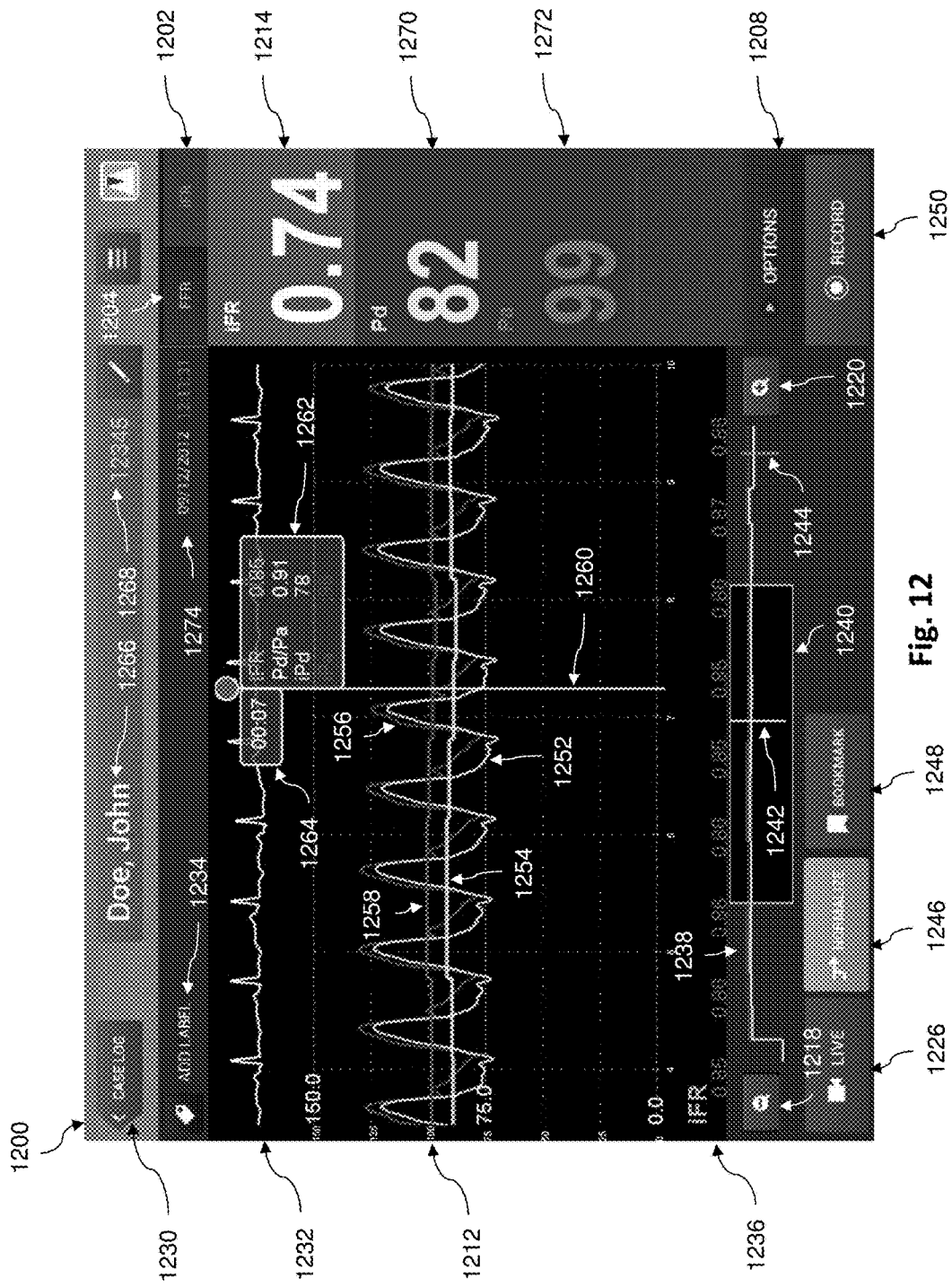
FIG. 12 shows a screen display according to an embodiment of the present disclosure.

Referring now to FIGS. 12-16, shown therein are various visual depictions of screen displays for evaluating a vessel based on obtained pressure measurements according to embodiments of the present disclosure. The screen displays are displayed on a touch-sensitive display of a bedside controller. A clinician can view, analyze, and interact with the pressure data and/or visual representations of the pressure data. Referring more specifically to FIG. 12, shown therein is a screen display 1200 according to an embodiment of the present disclosure. As illustrated, the screen display 1200 is associated with an iFR workflow. The screen display 1200 includes an FFR tab 1204 and an iFR tab 1202. The iFR tab 1202 can include the obtained pressure measurements, and visual representations of the pressure measurements. As shown, the iFR tab 1202 includes pressure waveform plots 1212 and 1238, both of which illustrate acquired pressure data over the same time period. The screen display 1200 also includes a window 1214 that shows a calculated pressure ratio (e.g., FFR, iFR, or otherwise).

In that regard, the pressure waveform plots 1212 and 1238 and the calculated pressure ratio of screen display 1200 illustrate aspects of pressure measurements obtained as one instrument is moved through the vessel and another instrument is maintained at a fixed location. In that regard, in some instances the pressure measurements are representative of a pressure ratio between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer to the fixed position of the proximal pressure measurement). For clarity in understanding the concepts of the present disclosure, this arrangement will be utilized to describe many of the embodiments of the present disclosure. However, it is understood that the concepts are equally applicable to other arrangements. For example, in some instances, the instrument is pushed through the vessel from a first position distal of the proximal pressure measurement location to a second position further distal (i.e., further away from the fixed position of the proximal pressure measurement). In other instances, a distal pressure measurement is obtained at a fixed location within the vessel and the instrument is pulled back through the vessel from a first position proximal of the fixed location of the distal pressure measurement to a second position more proximal than the first position (i.e., further away from the fixed position of the distal pressure measurement). In still other instances, a distal pressure measurement is obtained at a fixed location within the vessel and the instrument is pushed through the vessel from a first position proximal of the fixed location of the distal pressure measurement to a second position less proximal than the first position (i.e., closer the fixed position of the distal pressure measurement).

The pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances. In some instances, the pressure differential is calculated for each heartbeat cycle of the patient. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances.

In some embodiments a diagnostic window is selected using one or more of the techniques described in U.S. patent application Ser. No. 13/460,296, filed Apr. 30, 2012, now published as U.S. Patent Application Publication No. 2013-0046190 A1 on Feb. 21, 2013 and titled "DEVICES, SYSTEMS, AND METHODS FOR ASSESSING A VESSEL," which is hereby incorporated by reference in its entirety. As discussed therein, the diagnostic windows and associated techniques are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

The visual representations in the screen display 1200 illustrate the pressure ratio and/or the underlying pressure measurements in any suitable way. Generally speaking, the representation of the data can be utilized to identify gradients/changes in the pressure ratio and/or the underlying pressure measurements that can be indicative of a significant lesion in the vessel. In that regard, the visual representation of the data can include the pressure measurement(s); a ratio of the pressure measurements; a difference in the pressure measurements; a gradient of the pressure measurement(s), the ratio of the pressure measurements, and/or the difference in the pressure measurements; first or second derivatives of the pressure measurement(s), the ratio of the pressure measurements, and/or the difference in the pressure measurements; and/or combinations thereof.

For example, the pressure waveform plots 1212 and 1238 show corresponding pressure data. In that regard, the pressure waveform plots 1212 and 1238 can include the pressure waveform for the pressure sensing device moved through the vessel during the pullback, the pressure waveform for the stationary pressure sensing device, or both. In the illustrated embodiment, the pressure waveform plots 1212 and 1238 include the pressure waveforms for both. As will be discussed below with respect to FIGS. 14-16, in some instances the pressure waveform plot 1212 is augmented to highlight or otherwise accentuate the pressure data corresponding to the diagnostic window utilized for the pressure ratio calculations.

The pressure waveform plots 1212 and 1238 include time on the x-axis and magnitude of pressure on the y-axis. The pressure waveform plot 1238 illustrates the obtained pressure measurements over a greater amount of time compared to the waveform plot 1212. For example, the pressure waveform plot 1238 illustrates the entire acquisition, pullback, or "run" while the pressure waveform 1212 illustrates at least a portion thereof. The pressure waveform plot 1212 includes a curve 1256 that is representative of the pressure measured by the instrument maintained at a fixed location (for sake of brevity, this will be referred to as Pa below) and a curve 1252 that is representative of the pressure measured by the instrument moved through the vessel for the pullback over time (for sake of brevity, this will be referred to as Pd below). The pressure waveform plot 1212 also includes the averages of the acquired Pa and Pd values. The curve 1254 is representative of the average Pd values, while the curve 1258 is representative of the average Pa values. In that regard, the average Pa and Pd values can be a mean, median, mode, and/or other suitable value (e.g., filtering to remove outliers, then using mean, median, and/or mode, etc.) for each heartbeat cycle. In some embodiments, the pressure waveform plot 1212 includes all four curves 1252, 1254, 1256, and 1258. In some embodiments, the pressure waveform plot 1212 includes a subset (e.g., one or more, but not all) of the curves 1252, 1254, 1256, and 1258. For example, the pressure waveform plot 1212 can illustrate only the acquired Pa and Pd values by including the curves 1242 and 1256, or only the average Pa and Pd values by including the curves 1254 and 1258. The pressure waveform plot 1238 can similarly illustrate one or more of the curves 1252, 1254, 1256, and 1258 over the entire acquisition. In FIG. 12, the pressure waveform plot 1212 includes all four curves 1252, 1254, 1256, and 1258, while the pressure waveform plot 1238 includes the average Pa and Pd values. The pressure waveform plots 1212 and 1238 can include raw pressure data and/or data that smoothed, filtered, conditioned, and/or otherwise treated to remove abnormalities in the data as described in U.S. Provisional Patent Application No. 61/856,518, filed Jul. 19, 2013, now published as U.S. Patent Application Publication No. 2015/0025398 A1 on Jan. 22, 2015 and titled "DEVICES, SYSTEMS, AND METHODS FOR ASSESSING A VESSEL WITH AUTOMATED DRIFT CORRECTION," which is hereby incorporated by reference in its entirety. A normalize option 1246 can be provided to perform a normalization procedure described in U.S. application Ser. No. 14/157,404, filed Jan. 16, 2014, now published as U.S. Patent Application Publication No. 2014/0135633 A1 on May 15, 2014 and titled "DEVICES, SYSTEMS, AND METHODS FOR ASSESSING A VESSEL," which is hereby incorporated by reference herein, in its entirety.

A graphical overlay 1240 overlay can be positioned over a portion of the pressure waveform plot 1238. The overlay 1240 illustrates a portion of the obtained pressure measurements represented in the pressure waveform plot 1212. Thus, for example, the pressure waveform plot 1212 is a "zoomed in" version of the pressure waveform plot 1238 in that the pressure waveform plot 1212 covers a shorter acquisition period but includes more detail about the pressure measurements during that selected time period. A user can interact with the pressure data by, e.g., touch and dragging the overlay 1240 and or the pressure waveform plot 1212 to the left or right, on the touch-sensitive display of the bedside controller, to view other portions of the acquisition. The screen display 1200 can automatically update, in real time, as the user clicks and drags the overlay 1240. For example, the screen display 1200 can be automatically modified as the overlay 1240 shifts position over the pressure waveform plot 1238 and as the pressure waveform plot 1212 updates to include pressure data collected over the selected time period. The screen display 1200 also includes zoom buttons 1218, 1220 that allow a user to zoom out or in, respectively, on the pressure waveform plot 1212. The screen display 1200 can automatically update the pressure waveform plot 1212 to include the appropriate portions of pressure data, and the width and/or the position of the overlay 1240 over the pressure waveform plot 1238 in response to the user touch inputs on the zoom buttons 1218, 1220.

The screen display 1200 can include a visual representation of the acquired pressure measurements at a particular time. For example, a user can touch and release at a point on the pressure waveform plot 1212, on touch-sensitive display of the bedside controller. The selected point or location in the plot 1212 corresponds to a particular time during the acquisition. As shown in FIG. 12, a user provides a touch input near seven seconds on the pressure waveform plot 1212. In response to the user touch input, the screen display 1200 can be modified to include one or more information overlays 1260, 1262, and/or 1264. The overlay 1260 is a vertical line highlighting the time selected by the user by the touch input. The overlay 1260 can be variously colored to visually distinguish the selected time. The overlay 1264 provides the numerical value of the time that is selected by the user touch input. The overlay 1262 provides pressure data at the selected time. In that regard, the overlay 1262 can include a numerical value of a calculated pressure ratio (iFR, FFR, etc.) at the selected time, a numerical value of a compensated Pd/Pa at the selected time, a numerical value of the average Pd value at the selected time, a numerical value of the average Pa value at the selected time, a numerical value of the actual Pd value at the selected time, and/or a numerical value of the actual Pd value at the selected time. The numerical values in the overlay 1262 can be raw or modified values. When a particular time is highlighted in response to a user touch input in the pressure waveform plot 1212, the screen display 1200 can be automatically modified to include a corresponding overlay 1242 in the pressure waveform plot 1238 to contextualize the highlighted time within the entire acquisition. As described with respect to FIG. 13, some embodiments of the screen display can include a fixed indicator 1244 in one or both of the pressure waveform plots 1212 and 1238, which highlights a particular fixed time in the acquisition (e.g., a time associated with maximal hyperemia, at which point FFR is calculated). In some embodiments, the overlay(s) highlighting the selected time can be removed in response to a user touch input on the bedside controller.

The screen display 1200 also provides pressure ratios 1236 (e.g., iFR, compensated Pa/Pd values, etc.) at fixed intervals. For example, in FIG. 12, the iFR values 1236 for each heartbeat cycle are displayed below the pressure waveform plot 1212. In other embodiments, the pressure ratios are displayed at various locations relative to the pressure waveform plot 1212, such as proximate the curve 1252, 1254, 1256, and/or 1258.

The screen display 1200 also includes a window 1214 that shows a calculated pressure ratio (e.g., FFR, iFR, or otherwise). In the illustrated embodiment of FIG. 12, the window 1214 shows an iFR pressure ratio value during a pullback. In that regard, the iFR pressure ratio and/or associated data may be calculated and/or displayed as described in one or more of PCT Patent Application Publication No. WO 2012/093260, filed Jan. 6, 2012 and titled "APPARATUS AND METHOD OF CHARACTERISING A NARROWING IN A FLUID FILLED TUBE," PCT Patent Application Publication No. WO 2012/093266, filed Jan. 6, 2012 and titled "APPARATUS AND METHOD OF ASSESSING A NARROWING IN A FLUID FILLED TUBE," U.S. patent application Ser. No. 13/460,296, filed Apr. 30, 2012, now published as U.S. Patent Application Publication No. 2013-0046190-A1 on Feb. 21, 2013, and titled "DEVICES, SYSTEMS, AND METHODS FOR ASSESSING A VESSEL," PCT Patent Application Publication No. WO 2013/028612, filed Aug. 20, 2012 and titled "DEVICES, SYSTEMS, AND METHODS FOR VISUALLY DEPICTING A VESSEL AND EVALUATING TREATMENT OPTIONS," U.S. Provisional Patent Application No. 61/856,509, filed Jul. 19, 2013, now published as U.S. Patent Application Publication No. 2015-0025330 A1 on Jan. 22, 2015, and titled "DEVICES, SYSTEMS, AND METHODS FOR ASSESSMENT OF VESSELS," and U.S. Provisional Patent Application No. 61/856,518, filed Jul. 19, 2013, now published as U.S. Patent Application Publication No. 2015/0025398 A1 on Jan. 22, 2015 and titled "DEVICES, SYSTEMS, AND METHODS FOR ASSESSING A VESSEL WITH AUTOMATED DRIFT CORRECTION," each of which is hereby incorporated by reference in its entirety. In some instances, the numerical value of the pressure ratio displayed in window 1214 is updated based on portion of pressure data displayed the pressure waveform plot 1212 and/or the position of the overlay 1240 over the pressure waveform plot 1238. In that regard, in some instances the numerical value of the pressure ratio displayed in window 214 is based solely on the pressure data being displayed in the pressure waveform plot 1212. However, in other instances the numerical value of the pressure ratio displayed in window 214 is based one of or a combination of the pressure data being displayed in the plot 1212 and pressure data not displayed in the pressure waveform plot 1212. For example, the pressure ratio displayed in the window 214 can be based on the entire acquisition (as illustrated by the pressure waveform plot 1240, in some embodiments). The screen display 1200 also includes windows 1270 and 1272 that show the Pd and Pa values, respectively, used to calculate the pressure ratio shown in window 1214.

As shown in FIG. 12, the screen display 1200 provided on the touch-sensitive display of the bedside controller includes a button 1226 indicating that the data is being displayed in a "Live" mode, which indicates that the screen display 1200, including pressure waveform plots 1212 and 1238, calculated pressure ratios 1236, and/or the windows 1214, 1270, 1272 are being updated in real time as a procedure is being performed. The record button 1250 can be selected by a user touch input on the bedside controller to begin storing the acquired pressure data. In other instances, the button 1226 of the screen display 1200 will indicated that it is in "Playback" or "Review" mode, which indicates that the screen display 1200 is showing data obtained previously. With respect to the "Live" mode, it should be noted that the determination of the diagnostic window and/or the calculation of the pressure differential are performed in approximately real time or live to identify the diagnostic window of the heartbeat cycle and calculate the pressure differential. In that regard, calculating the pressure differential in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure differential calculation is performed 10 or more seconds after data acquisition. For example, in some embodiments, the data utilized to identify the diagnostic window and/or calculate the pressure differential are stored for later analysis.

By comparing the calculated pressure differential to a threshold or predetermined value, a physician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

In that regard, the coloring and/or other visually distinguishing aspect of the pressure differential measurements depicted in pressure ratios 1236 and/or window 1214 of the screen display 1200 of FIG. 12 are configured based on the threshold value in some instances. For example, a first color (e.g., green, white, or otherwise) can be utilized to represent values well above the threshold value (e.g., where the threshold value is 0.80 on a scale of 0.00 to 1.00, values above 0.90), a second color (e.g., yellow, gray, or otherwise) can be utilized to represent values near but above the threshold value (e.g., where the threshold value is 0.80 on a scale of 0.00 to 1.00, values between 0.81 and 0.90), and a third color (e.g., red, black, or otherwise) can be utilized to represent values equal to or below the threshold value (e.g., where the threshold value is 0.80 on a scale of 0.00 to 1.00, values of 0.80 and below). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

The screen display 1200 includes an ECG waveform 1232. The ECG waveform can be temporally synced with the pressure waveform plots 1212 and/or 1238. In that regards, the ECG waveform 1232 can be modified in response to modifications of the pressure waveform plots 1212 and/or 1238. For example, the ECG waveform 1232 can be "zoomed in" or "zoomed in" when a user views different portions of the pressure waveform plots 1212 and/or 1238 such that the times in the ECG waveform 1232 and the pressure waveform plots 1212 and 1238 are synced. The screen display 1200 additionally includes a patient name 1266, patient identifier 1268, and a date/time 1274. The case log button 1200 can be selected access additional information about the patient (e.g., other pressure acquisitions) and/or retrieve the current pressure acquisition data at a later time. A label field 1234 allows the user to input additional notes regarding the patient or the procedure. Selecting the label field 1266 by a touch input on the bedside controller can cause an on-screen keyboard to be displayed. The user can input characters into the label field 1266 by touch inputs on the on-screen keyboard. The screen display also includes an options tab 1208 and a bookmark option 1248, which described in greater detail with respect to FIG. 13.

Figure 13:
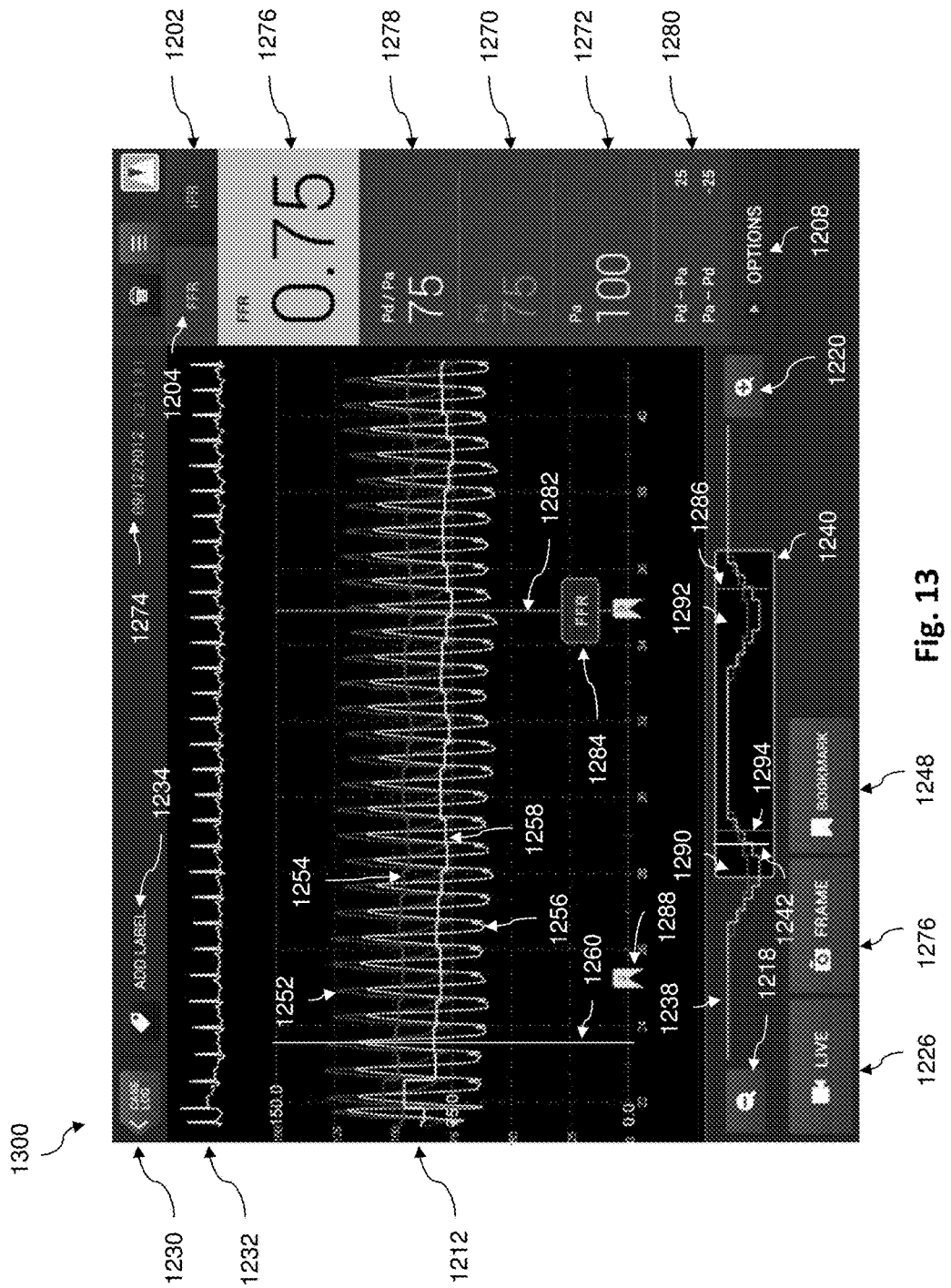
FIG. 13 shows a screen display according to an embodiment of the present disclosure.

Referring now to FIG. 13, shown therein a screen display 1300 according to an embodiment of the present disclosure. The screen display 1300 is similar in many respects to screen display 1200 described above. In that regard, one or more features of screen display 1200 can be included in the screen display 1300 (e.g., the overlays 1262 and/or 1264). However, the screen display 1300 is associated with an FFR workflow. In that regard, a hyperemic agent can be administrated to the patient at two intervals 1290 and 1292, as illustrated in the pressure waveform plot 1238. The FFR tab 1204 can include the obtained pressure measurements and visual representations of the pressure measurements. In that regard, the FFR tab 1204 is includes a window 1276 that shows a numerical value of the calculated pressure ratio (e.g., FFR, iFR, or otherwise) as well as windows 1270 and 1272 that show the numerical values of the average Pd and Pa at maximum hyperemia, which are used to calculate FFR.

The screen display 1300 can also include a window 1278 that shows the numerical compensated Pd/Pa value and/or a window 1280 that includes one or both of the numerical differences between Pd and Pa (e.g., Pd—Pa and/or Pa—Pd).

The pressure waveform plot 1212 can include one or both of overlays 1282 and 1284 that highlight the time during the acquisition corresponding to maximum hyperemia. The time at which maximum hyperemia can be automatically determined by the processing system. A time at which maximum hyperemia occurs can be determined for each hyperemia interval 1290 and 1292. The overlay 1282 is vertical line highlighting the time at which hyperemia occurred during the hyperemia interval 1292. The overlay 1282 can be variously colored to visually distinguish the selected time. For example, the overlay 1282 can be differently colored than the overlay 1260, which is a user highlighted time during the acquisition, as described above with respect to FIG. 12. The average Pa and Pd values at the determined time of maximum hyperemia are used to calculate the FFR for the interval 1292. The overlay 1284 is a textual indicator that that specifies that the FFR is calculated based on average Pa and Pd values at the highlighted time. The pressure waveform plot 1238 includes an overlay 1286 contextualizing the time(s) during the acquisition when maximum hyperemia occurs for the interval 1292 and an overlay 1294 indicating when maximum hyperemia occurs for the interval 1290. The pressure waveform plot 1238 also includes the overlay 1242 that highlights the user-selected time. As with the overlays 1260 and 1282 in the pressure waveform plot 1212, the overlay 1242 is colored differently than the overlays 1286 and 1292 in pressure waveform 1238. The overlays 1282, 1286, and/or 1294 can be positioned at fixed locations in the waveforms 1212 and/or 1238, which correspond to the determined times at which maximum hyperemia occur in the intervals 1290 and 1292. The overlays 1242 and/or 1260 can be selectively added or removed in response to a user's touch input at any location in the waveforms 1212 and/or 1238, which corresponding to any time during the acquisition.

The pressure waveform plot 1212 in screen display 1300 includes a bookmark 1288. The bookmark 1288 can be added during "Live" or "Review" mode when a user touches and releases the bookmark option 1248 on the touch-sensitive display of the bedside controller. The bookmark can highlight a time during the acquisition that a clinician is interested in later reviewing in more detail. For example, a clinician can touch and release the pressure waveform 1212 at the point corresponding to the bookmark 1288 such that, e.g., the overlay 1262 providing pressure data at the selected time is displayed on the bedside controller. In some embodiments, touching and release the bookmark 1288 can cause the overlay 1262 to be displayed. In some embodiments the screen display 1300 includes a screenshot option 1276 for the user to take a picture of the screen display in its current form. The screenshot can be saved in a memory of the bedside controller and later accessed by the user by selecting, e.g., the case log 1230.

Figure 14:
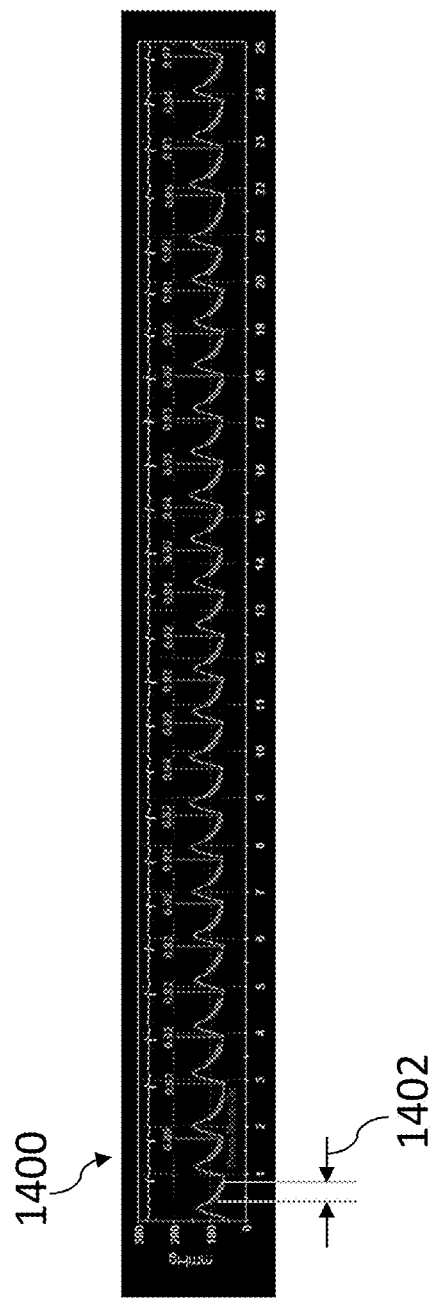
FIG. 14 shows a portion of a screen display according to another embodiment of the present disclosure.
Figure 15:
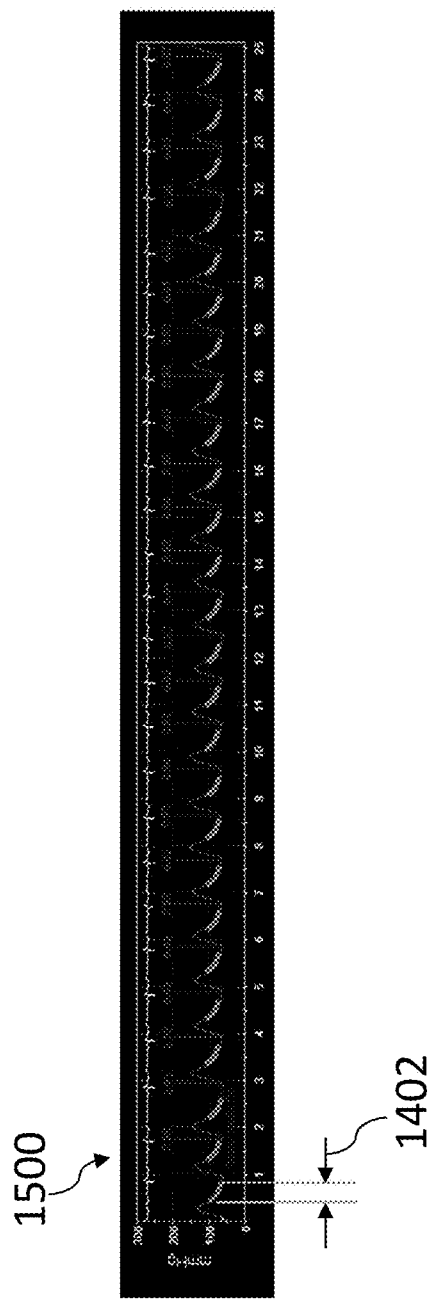
FIG. 15 shows a portion of a screen display according to another embodiment of the present disclosure.
Figure 16:
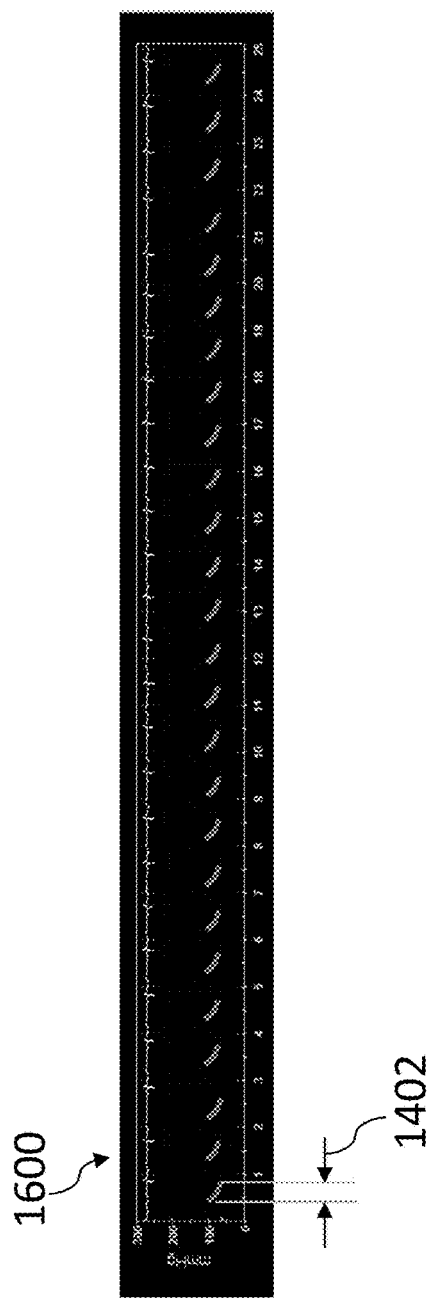
FIG. 16 shows a portion of a screen display according to another embodiment of the present disclosure.

Referring generally to FIGS. 14-16, shown therein are additional visual representations of pressure measurements that can be provided in addition to and/or in lieu of the elements of screen displays 1200 and 1300. In that regard, the screen displays 1200 and 1300 can include one or more features described in U.S. Provisional Application No. 61/942,338, filed Feb. 20, 2014, now published as U.S. Patent Application Publication Nos. 2015-0230713 A1 on Aug. 20, 2015, and 2015-0238096 A1 on Aug. 27, 2015 titled "Devices, Systems, and Methods and Associated Display Screens for Assessment of Vessels" and U.S. Provisional Application No. 62/024,901, titled "Devices, Systems, and Methods and Associated Display Screens for Assessment of Vessels with Multiple Sensing Components" and filed Jul. 15, 2014, both of which are hereby incorporated by reference herein in their entireties. For example, the screen displays 1200 and 1300 can include numerical, visual, and/or graphical representations of an pressure ratio (iFR, FFR, compensated Pa/Pd, etc.) over time, a pressure difference during a pullback, a cumulative change in a pressure ratio value over time during a pullback, a localized change in pressure ratio value over time, Pa and Pd pressures over time during a pullback, pressure measurements obtained from multiple distal pressure sensing components over time as part of a virtual pullback, an enhanced angiographic image of a vessel based on overlaid intravascular measurements, etc. The screen displays can be provided to the bedside controller where a user can view and interact with the data with touch inputs on the touch-sensitive display.

Referring now to FIGS. 14-16, shown therein are various displays of pressure waveform plots according to the present disclosure. In particular, the embodiments of FIGS. 14-16 may be used in place of the pressure waveform plot 1212 and/or 1238 in any of the screen displays of the present disclosure. To that end, the pressure waveform plots of FIGS. 14-16 highlight, emphasis, and/or otherwise accentuate the portion(s) of the pressure data utilized in making the pressure ratio calculations depicted in the other graphs and/or windows of the screen displays. In particular, in some implementations the pressure waveform plots of FIGS. 14-16 identify the diagnostic window utilized in making iFR calculations.

Referring more specifically to FIG. 14, shown therein is a pressure waveform plot 100 that corresponds to similar data as shown in pressure waveform plot 1212 of FIG. 12, but where the pressure data for each heartbeat that is within the diagnostic window utilized for making the iFR calculations shown in window 1214 has been highlighted. For example, for the first heartbeat cycle on the left side of the pressure waveform plot 1400, the pressure data within a diagnostic window 1402 has been highlighted. By highlighting the portions of the pressure waveform plot 1400 within the diagnostic window for each heartbeat cycle, a user can quickly visualize the pressure data being relied upon for the resulting pressure ratio calculations.

FIGS. 15 and 16 illustrate other ways of identifying the portions of the pressure waveform plot within the diagnostic window for each heartbeat cycle. For example, FIG. 15 shows a pressure waveform plot 1500 that corresponds to the similar data as shown in pressure waveform plots 1212 and 1400 above, but where the pressure data for each heartbeat that is within the diagnostic window utilized for making the iFR calculations shown window 1214 has been highlighted and the pressure data for each heartbeat that is outside of the diagnostic window has been faded. In particular, for the first heartbeat cycle on the left side of the pressure waveform plot 1500, the pressure data within the diagnostic window 1402 has been highlighted and the remaining pressure data for the first heartbeat cycle is shown in faded or other low contrast setting. Similarly, FIG. 16 shows a pressure waveform plot 1600 that corresponds to the same data as shown in pressure waveform plots 1212, 1400, and 1500 above, but where the pressure data for each heartbeat that is within the diagnostic window utilized for making the iFR calculations shown in window 1214 has been highlighted and the pressure data for each heartbeat that is outside of the diagnostic window has been removed entirely. In particular, for the first heartbeat cycle on the left side of the pressure waveform plot 1600, the pressure data within the diagnostic window 1402 has been highlighted and the remaining pressure data for the first heartbeat cycle has been removed. Accordingly, the pressure waveform plot 1600 only shows the pressure data within the diagnostic window 1402. It is understood that the pressure data within the diagnostic window can be identified and/or accentuated in any suitable manner.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of evaluating a vessel of a patient, comprising:
    obtaining pressure measurements from a first instrument and a second instrument positioned within the vessel of the patient while the second instrument is moved longitudinally through the vessel from a distal position in the vessel to a proximal position in the vessel and the first instrument remains stationary within the vessel;
    outputting, to a touch-sensitive display of a bedside controller, a screen display including:
        a visual representation of a first pressure ratio of the pressure measurements;
        a first proximal pressure waveform, a first distal pressure waveform, a second proximal pressure waveform, and a second distal pressure waveform, wherein the first proximal pressure waveform, the first distal pressure waveform, the second proximal pressure waveform, and the second distal pressure waveform are representative of the obtained pressure measurements, and wherein the second proximal and distal pressure waveforms illustrate the pressure measurements obtained over a greater amount of time compared to the first proximal and distal pressure waveforms; and
        an overlay positioned over a portion of the second proximal and distal pressure waveforms, the overlay identifying a first portion of the obtained pressure measurements represented in the first proximal and distal pressure waveforms;
    receiving, through the touch-sensitive display of the bedside controller, a user touch input modifying the overlay to identify a second portion of the pressure measurements; and
    modifying the screen display, in response to the user touch input, to illustrate the second portion of the pressure measurements in the first proximal and distal pressure waveforms.

2. The method of claim 1,
    wherein modifying the overlay comprises moving the overlay to be positioned over a different portion of the second proximal and distal pressure waveforms, and wherein modifying the screen display comprises modifying the screen display, in response to the user touch input, such that the first proximal and distal pressure waveforms include the obtained pressure measurements corresponding to the position of the overlay over the different portion of the second proximal and distal pressure waveforms.

3. The method of claim 1, wherein the screen display includes numerical values of the obtained pressure measurements.

4. The method of claim 1, wherein the visual representation of a first pressure ratio of the obtained pressure measurements includes a numerical value.

5. The method of claim 4, wherein the screen display includes a second pressure ratio of the obtained pressure measurements, wherein the second pressure ratio is calculated differently than the first pressure ratio.

6. The method of claim 1, wherein the screen display includes a visual representation of a difference in the pressure measurements.

7. A method of evaluating a vessel of a patient, comprising:
obtaining pressure measurements from a first instrument and a second instrument positioned within the vessel of the patient while the second instrument is moved longitudinally through the vessel from a distal position in the vessel to a proximal position in the vessel and the first instrument remains stationary within the vessel;
outputting, to a touch-sensitive display of a bedside controller, a screen display including:
a first proximal pressure waveform and a first distal pressure waveform, wherein the first proximal pressure waveform and the first distal pressure waveform are representative of the obtained pressure measurements; and
a plurality of pressure ratios of the obtained pressure measurements, each of the plurality of pressure ratios separated by a fixed interval;
receiving, through the touch-sensitive display of the bedside controller, a user touch input; and
modifying the screen display in response to the user touch input.

8. The method of claim 7, further comprising:
receiving, through the touch-sensitive display of the bedside controller, a further user touch input identifying a time at which pressure measurements were obtained; and
modifying, in response to the further user touch input, the screen display to include a visual representation of the obtained pressure measurements corresponding to the identified time.

9. The method of claim 8, wherein the visual representation of the obtained pressure measurements corresponding to the identified time is displayed at a location proximate the at least a portion of the first pressure waveform defined by a point of initial contact with the touch-sensitive display.

10. The method of claim 9, wherein the visual representation of the obtained pressure measurements corresponding to the identified time includes a numerical value of the obtained pressure measurements at the identified time.

11. The method of claim 9, wherein visual representation of the obtained pressure measurements corresponding to the identified time includes a first pressure ratio of the obtained pressure measurements at the identified time.

12. The method of claim 11, wherein the visual representation of the obtained pressure measurements corresponding to the identified time includes a second pressure ratio of the obtained pressure measurements at the identified time, wherein the second pressure ratio is calculated differently than the first pressure ratio.

13. The method of claim 9, wherein the visual representation of the obtained pressure measurements corresponding to the identified time includes a numerical value of the obtained pressure measurements at the identified time, a first pressure ratio of the obtained pressure measurements at the identified time, and a second pressure ratio of the obtained pressure measurements at the identified time, wherein the second pressure ratio is calculated differently than the first pressure ratio.

14. A system for evaluating a vessel of a patient, comprising:
a first instrument sized and shaped for introduction into the vessel of the patient;
a second instrument sized and shaped for introduction into the vessel of the patient, wherein the second instrument is configured to move longitudinally through the vessel from a distal position in the vessel to a proximal position in the vessel while the first instrument remains stationary within the vessel;
a bedside controller comprising a touch-sensitive display, the bedside controller being configured to display a screen display and to receive user touch inputs on the touch-sensitive display; and
a processing system communicatively coupled to the first and second instruments and the bedside controller, the processing system configured to:
receive pressure measurements from the first and second instruments;
output, to the touch-sensitive display of the bedside controller, the screen display including:
a first proximal pressure waveform and a first distal pressure waveform, wherein the first proximal pressure waveform and the first distal pressure waveform are representative of the obtained pressure measurements; and
a plurality of pressure ratios of the obtained pressure measurements, each of the plurality of pressure ratios separated by a fixed interval;
receive a signal from the bedside controller in response to a user touch input received at the touch-sensitive display; and
modify the screen display in response to the received signal.

15. The system of claim 14, wherein the processing system is configured to:
receive a further signal in response to a further user touch input identifying a time at which the pressure measurements were obtained; and
modify the screen display, in response to the received further signal, to include a visual representation of the obtained pressure measurements corresponding to the identified time.

16. The system of claim 15, wherein the visual representation of the obtained pressure measurements corresponding to the identified time includes a numerical value of the obtained pressure measurements at the identified time and a numerical value of a first pressure ratio of the obtained pressure measurements at the identified time.

17. The system of claim 16, wherein the visual representation of the obtained pressure measurements corresponding to the identified time further includes a numerical value of a second pressure ratio of the obtained pressure measurements at the identified time, wherein the second pressure ratio is calculated differently than the first pressure ratio.

18. A system for evaluating a vessel of a patient, comprising:
- a first instrument sized and shaped for introduction into the vessel of the patient;
- a second instrument sized and shaped for introduction into the vessel of the patient, wherein the second instrument is configured to move longitudinally through the vessel from a distal position in the vessel to a proximal position in the vessel while the first instrument remains stationary within the vessel;
- a bedside controller comprising a touch-sensitive display, the bedside controller being configured to display a screen display and to receive user touch inputs on the touch-sensitive display; and
- a processing system communicatively coupled to the first and second instruments and the bedside controller, the processing system configured to:
  - receive pressure measurements from the first and second instruments:
  - output, to the touch-sensitive display of the bedside controller, the screen display including:
    - a visual representation of a pressure ratio of the pressure measurements;
    - a first proximal pressure waveform, a first distal pressure waveform, a second proximal pressure waveform, and a second distal pressure waveform, wherein the first proximal pressure waveform, first distal pressure waveform, the second proximal pressure waveform, and the second distal pressure waveform are representative of the obtained pressure measurements, and wherein the second proximal and distal pressure waveforms illustrate the pressure measurements obtained over a greater amount of time compared to the first proximal and distal pressure waveforms; and
    - an overlay positioned over a portion of the second proximal and distal pressure waveforms, the overlay identifying a first portion of the pressure measurements represented in the first proximal and distal pressure waveforms;
  - receive a signal from the bedside controller in response to a user touch input received at the touch-sensitive display, the user touch input modifying the overlay to identify a second portion of the pressure measurements; and
  - modify the screen display, in response to the received signal, to illustrate the second portion of the pressure measurements in the first proximal and distal pressure waveforms.

19. The system of claim 18, wherein modifying the overlay comprises moving the overlay to be positioned over a different portion of the second proximal and distal pressure waveforms; and
- wherein modifying the screen display comprising modifying the screen display, in response to the received signal, such that the first proximal and distal pressure waveforms include the obtained pressure measurements corresponding to the position of the overlay over the different portion of the second proximal and distal pressure waveforms.

20. The system of claim 18,
- wherein the first proximal and distal pressure waveforms comprise a plot of measured pressure values and/or average pressure values, and
- wherein the second proximal and distal pressure waveforms comprise a plot of measured pressure values and/or average pressure values.

* * * * *